(12) United States Patent
Reggiardo et al.

(10) Patent No.: US 8,579,853 B2
(45) Date of Patent: Nov. 12, 2013

(54) INFUSION DEVICES AND METHODS

(75) Inventors: Christopher V. Reggiardo, Castro Valley, CA (US); Namvar Kiaie, Danville, CA (US); James Thomson, Alameda, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 11/555,207

(22) Filed: Oct. 31, 2006

(65) Prior Publication Data

US 2008/0103447 A1    May 1, 2008

(51) Int. Cl.
*A61M 31/00* (2006.01)

(52) U.S. Cl.
USPC .............................. 604/65; 604/226; 604/232

(58) Field of Classification Search
USPC ........................................... 604/65, 226, 232
See application file for complete search history.

(56) References Cited

U.S. PATENT DOCUMENTS

| | | | |
|---|---|---|---|
| 2,508,253 A | 5/1950 | Haggardt |
| 2,915,579 A | 12/1959 | Mendelsohn |
| 3,374,337 A | 3/1968 | Burley |
| 3,510,747 A | 5/1970 | Petrides |
| 3,541,892 A | 11/1970 | Kubinek et al. |
| 3,606,592 A | 9/1971 | Madurski et al. |
| 3,750,687 A | 8/1973 | Williams |
| 3,843,455 A | 10/1974 | Bier |
| 3,923,060 A | 12/1975 | Ellinwood |
| 3,930,493 A | 1/1976 | Williamson |
| 3,938,140 A | 2/1976 | Garcia et al. |
| 3,994,799 A | 11/1976 | Yao et al. |
| 4,018,547 A | 4/1977 | Rogen |
| 4,048,551 A | 9/1977 | Bosik |
| 4,121,282 A | 10/1978 | Ohsawa |
| 4,146,029 A | 3/1979 | Ellinwood |
| 4,172,770 A | 10/1979 | Semersky et al. |
| 4,193,397 A | 3/1980 | Tucker et al. |
| 4,268,173 A | 5/1981 | Barnard et al. |
| 4,288,793 A | 9/1981 | Lotscher |
| 4,309,156 A | 1/1982 | Gonner et al. |
| 4,360,019 A | 11/1982 | Potner et al. |
| 4,362,052 A | 12/1982 | Heath et al. |
| 4,401,122 A | 8/1983 | Clark, Jr. |
| 4,439,197 A | 3/1984 | Honda et al. |
| 4,441,968 A | 4/1984 | Emmer et al. |
| 4,447,224 A | 5/1984 | DeCant, Jr. et al. |
| 4,458,686 A | 7/1984 | Clark, Jr. |
| 4,467,811 A | 8/1984 | Clark, Jr. |

(Continued)

FOREIGN PATENT DOCUMENTS

| CA | 2143172 | 7/2005 |
|---|---|---|
| EP | 0455455 | 11/1991 |

(Continued)

OTHER PUBLICATIONS

"An Electrochemical Slow Flow Meter", http://gore.ocean.washington.edu/research/slow_flow_meter.html, 2005, 3 pages.

(Continued)

*Primary Examiner* — Nicholas Lucchesi
*Assistant Examiner* — Scott Medway
(74) *Attorney, Agent, or Firm* — Jackson & Co., LLP

(57) ABSTRACT

Medical devices having restrictive access, and methods thereof are provided.

29 Claims, 6 Drawing Sheets

(56) References Cited

U.S. PATENT DOCUMENTS

| | | |
|---|---|---|
| 4,472,113 A | 9/1984 | Rogen |
| 4,474,309 A | 10/1984 | Solomon |
| 4,486,190 A | 12/1984 | Reinicke |
| 4,494,950 A | 1/1985 | Fischell |
| 4,512,348 A | 4/1985 | Uchigaki et al. |
| 4,524,343 A | 6/1985 | Morgan et al. |
| 4,529,401 A | 7/1985 | Leslie et al. |
| 4,531,235 A | 7/1985 | Brusen |
| 4,562,751 A | 1/1986 | Nason et al. |
| 4,563,249 A | 1/1986 | Hale |
| 4,570,492 A | 2/1986 | Walsh |
| 4,573,994 A | 3/1986 | Fischell et al. |
| 4,574,809 A | 3/1986 | Talish et al. |
| 4,633,878 A | 1/1987 | Bombardieri |
| 4,655,880 A | 4/1987 | Liu |
| 4,678,408 A | 7/1987 | Nason et al. |
| 4,685,903 A | 8/1987 | Cable et al. |
| 4,686,624 A | 8/1987 | Blum et al. |
| 4,736,748 A | 4/1988 | Nakamura et al. |
| 4,755,173 A | 7/1988 | Konopka et al. |
| 4,811,564 A | 3/1989 | Palmer |
| 4,850,959 A | 7/1989 | Findl |
| 4,851,827 A | 7/1989 | Nicholas |
| 4,866,396 A | 9/1989 | Tamura |
| 4,883,409 A | 11/1989 | Strohmeier et al. |
| 4,890,621 A | 1/1990 | Hakky |
| 4,953,552 A | 9/1990 | DeMarzo |
| 4,976,590 A | 12/1990 | Baldwin |
| 4,979,509 A | 12/1990 | Hakky |
| 4,984,581 A | 1/1991 | Stice |
| 5,004,532 A | 4/1991 | Hale et al. |
| 5,012,667 A | 5/1991 | Kruse |
| 5,019,974 A * | 5/1991 | Beckers .......... 600/316 |
| 5,036,861 A | 8/1991 | Sembrowich et al. |
| 5,051,880 A | 9/1991 | Harm et al. |
| 5,061,914 A | 10/1991 | Bush et al. |
| 5,078,683 A | 1/1992 | Sancoff et al. |
| 5,079,920 A | 1/1992 | Whitehead et al. |
| 5,081,421 A | 1/1992 | Miller et al. |
| 5,101,814 A | 4/1992 | Palti |
| 5,124,661 A | 6/1992 | Zelin et al. |
| 5,139,023 A | 8/1992 | Stanley et al. |
| 5,155,695 A | 10/1992 | Stein |
| 5,190,041 A | 3/1993 | Palti |
| 5,205,819 A | 4/1993 | Ross et al. |
| 5,207,666 A | 5/1993 | Idriss et al. |
| 5,211,371 A | 5/1993 | Coffee |
| 5,211,626 A | 5/1993 | Frank et al. |
| 5,223,822 A | 6/1993 | Stommes et al. |
| 5,262,305 A | 11/1993 | Heller et al. |
| 5,264,104 A | 11/1993 | Gregg et al. |
| 5,267,026 A | 11/1993 | Kawahara et al. |
| 5,278,997 A | 1/1994 | Martin |
| 5,284,423 A | 2/1994 | Holdsworth et al. |
| 5,284,425 A | 2/1994 | Holtermann et al. |
| 5,291,614 A | 3/1994 | Baker et al. |
| 5,291,887 A | 3/1994 | Stanley et al. |
| 5,320,725 A | 6/1994 | Gregg et al. |
| 5,324,599 A | 6/1994 | Oyama et al. |
| 5,325,280 A | 6/1994 | Tortola et al. |
| 5,349,852 A | 9/1994 | Kamen et al. |
| 5,356,786 A | 10/1994 | Heller et al. |
| 5,366,292 A | 11/1994 | Voss |
| 5,368,028 A | 11/1994 | Palti |
| 5,371,687 A | 12/1994 | Holmes, II et al. |
| 5,372,133 A | 12/1994 | Esch |
| 5,376,070 A | 12/1994 | Purvis et al. |
| 5,382,331 A | 1/1995 | Banks |
| 5,390,671 A | 2/1995 | Lord et al. |
| 5,391,250 A | 2/1995 | Cheney, II et al. |
| 5,398,681 A | 3/1995 | Kupershmidt |
| 5,404,585 A | 4/1995 | Vimpari et al. |
| 5,406,301 A | 4/1995 | Ravid |
| 5,445,611 A | 8/1995 | Eppstein et al. |
| 5,448,992 A | 9/1995 | Kupershmidt |
| 5,458,140 A | 10/1995 | Eppstein et al. |
| 5,469,025 A | 11/1995 | Kanemori et al. |
| 5,479,486 A | 12/1995 | Saji |
| 5,494,562 A | 2/1996 | Maley et al. |
| 5,497,772 A | 3/1996 | Schulman et al. |
| 5,505,713 A | 4/1996 | Van Antwerp |
| 5,507,288 A | 4/1996 | Bocker et al. |
| 5,515,390 A | 5/1996 | Benton |
| 5,517,434 A | 5/1996 | Hanson et al. |
| 5,526,844 A | 6/1996 | Kamen et al. |
| 5,527,288 A | 6/1996 | Gross et al. |
| 5,533,389 A | 7/1996 | Kamen et al. |
| 5,543,678 A | 8/1996 | Hoiberg |
| 5,559,528 A | 9/1996 | Ravid |
| 5,568,400 A | 10/1996 | Stark et al. |
| 5,568,806 A | 10/1996 | Cheney, II et al. |
| 5,575,770 A | 11/1996 | Melsky et al. |
| 5,576,535 A | 11/1996 | Oosterwijk et al. |
| 5,586,553 A | 12/1996 | Halili et al. |
| 5,593,852 A | 1/1997 | Heller et al. |
| 5,594,906 A | 1/1997 | Holmes, II et al. |
| 5,596,261 A | 1/1997 | Suyama |
| 5,601,435 A | 2/1997 | Quy |
| 5,604,404 A | 2/1997 | Sahara |
| 5,615,671 A | 4/1997 | Schoonen et al. |
| 5,620,579 A | 4/1997 | Genshaw et al. |
| 5,622,413 A | 4/1997 | Kim et al. |
| 5,622,482 A | 4/1997 | Lee |
| 5,628,324 A | 5/1997 | Sarbach |
| 5,634,468 A | 6/1997 | Platt et al. |
| 5,640,954 A | 6/1997 | Pfeiffer et al. |
| 5,645,709 A | 7/1997 | Birch et al. |
| 5,660,163 A | 8/1997 | Schulman et al. |
| 5,661,643 A | 8/1997 | Blakely et al. |
| 5,662,461 A | 9/1997 | Ono |
| 5,665,222 A | 9/1997 | Heller et al. |
| 5,671,301 A | 9/1997 | Kupershmidt |
| 5,685,844 A | 11/1997 | Marttila |
| 5,695,949 A | 12/1997 | Galen et al. |
| 5,703,928 A | 12/1997 | Galloway et al. |
| 5,707,502 A | 1/1998 | McCaffrey et al. |
| 5,708,247 A | 1/1998 | McAleer et al. |
| 5,711,861 A | 1/1998 | Ward et al. |
| 5,711,868 A | 1/1998 | Maley et al. |
| 5,722,397 A | 3/1998 | Eppstein |
| 5,738,220 A | 4/1998 | Geszler |
| 5,741,211 A | 4/1998 | Renirie et al. |
| 5,748,872 A | 5/1998 | Norman |
| 5,759,510 A | 6/1998 | Pillai |
| 5,771,890 A | 6/1998 | Tamada |
| 5,774,254 A | 6/1998 | Berlin |
| 5,786,439 A | 7/1998 | Van Antwerp et al. |
| 5,790,297 A | 8/1998 | Berlin |
| 5,791,344 A | 8/1998 | Schulman et al. |
| 5,812,102 A | 9/1998 | Sprole et al. |
| 5,814,020 A | 9/1998 | Gross |
| 5,814,599 A | 9/1998 | Mitragotri et al. |
| 5,815,303 A | 9/1998 | Berlin |
| 5,822,715 A | 10/1998 | Worthington et al. |
| 5,825,488 A | 10/1998 | Kohl et al. |
| 5,848,990 A | 12/1998 | Cirelli et al. |
| 5,851,197 A | 12/1998 | Marano et al. |
| 5,856,631 A | 1/1999 | Julien |
| 5,858,001 A | 1/1999 | Tsals et al. |
| 5,873,026 A | 2/1999 | Reames |
| 5,875,417 A | 2/1999 | Golden |
| 5,885,211 A | 3/1999 | Eppstein et al. |
| 5,899,855 A | 5/1999 | Brown |
| 5,913,833 A | 6/1999 | Elstrom et al. |
| 5,918,603 A | 7/1999 | Brown |
| 5,919,167 A | 7/1999 | Mulhauser |
| 5,923,512 A | 7/1999 | Brownlow et al. |
| 5,931,814 A | 8/1999 | Alex et al. |
| 5,947,921 A | 9/1999 | Johnson et al. |
| 5,948,512 A | 9/1999 | Kubota et al. |
| 5,951,582 A | 9/1999 | Thorne et al. |
| 5,951,836 A | 9/1999 | McAleer et al. |
| 5,954,643 A | 9/1999 | Van Antwerp et al. |
| 5,965,380 A | 10/1999 | Heller et al. |

(56) References Cited

U.S. PATENT DOCUMENTS

| | | | |
|---|---|---|---|
| 5,968,011 | A | 10/1999 | Larsen et al. |
| 5,971,922 | A | 10/1999 | Arita et al. |
| 5,972,199 | A | 10/1999 | Heller et al. |
| 5,993,411 | A | 11/1999 | Choi |
| 5,994,878 | A | 11/1999 | Ostergaard et al. |
| 5,997,501 | A | 12/1999 | Gross et al. |
| 6,001,067 | A | 12/1999 | Shults et al. |
| 6,002,961 | A | 12/1999 | Mitragotri et al. |
| 6,011,486 | A | 1/2000 | Casey |
| 6,014,577 | A | 1/2000 | Henning et al. |
| 6,017,328 | A | 1/2000 | Fischell et al. |
| 6,018,678 | A | 1/2000 | Mitragotri et al. |
| 6,023,629 | A | 2/2000 | Tamada |
| 6,024,539 | A * | 2/2000 | Blomquist ............. 417/63 |
| 6,026,320 | A | 2/2000 | Carlson et al. |
| 6,027,459 | A | 2/2000 | Shain et al. |
| 6,027,496 | A | 2/2000 | Loomis et al. |
| 6,027,692 | A | 2/2000 | Galen et al. |
| 6,032,059 | A | 2/2000 | Henning et al. |
| 6,041,253 | A | 3/2000 | Kost et al. |
| 6,041,665 | A | 3/2000 | Hussain |
| 6,059,546 | A | 5/2000 | Brenan et al. |
| 6,063,039 | A | 5/2000 | Cunningham et al. |
| 6,064,368 | A | 5/2000 | Kang |
| 6,066,243 | A | 5/2000 | Anderson et al. |
| 6,067,017 | A | 5/2000 | Stewart et al. |
| 6,067,463 | A | 5/2000 | Jeng et al. |
| 6,071,249 | A | 6/2000 | Cunningham et al. |
| 6,071,251 | A | 6/2000 | Cunningham et al. |
| 6,073,031 | A | 6/2000 | Helstab et al. |
| 6,077,660 | A | 6/2000 | Wong et al. |
| 6,081,104 | A | 6/2000 | Kern |
| 6,082,289 | A | 7/2000 | Cavallaro |
| 6,083,710 | A | 7/2000 | Heller et al. |
| 6,085,871 | A | 7/2000 | Karamata |
| 6,086,575 | A | 7/2000 | Mejslov |
| 6,091,975 | A | 7/2000 | Daddona et al. |
| 6,093,156 | A | 7/2000 | Cunningham et al. |
| 6,093,172 | A | 7/2000 | Funderburk et al. |
| 6,103,033 | A | 8/2000 | Say et al. |
| 6,120,676 | A | 9/2000 | Heller et al. |
| 6,121,009 | A | 9/2000 | Heller et al. |
| 6,129,823 | A | 10/2000 | Hughes et al. |
| 6,132,371 | A | 10/2000 | Dempsey et al. |
| 6,134,461 | A | 10/2000 | Say et al. |
| 6,142,939 | A | 11/2000 | Eppstein et al. |
| 6,143,164 | A | 11/2000 | Heller et al. |
| 6,144,303 | A | 11/2000 | Federman |
| 6,144,869 | A | 11/2000 | Berner et al. |
| 6,144,922 | A | 11/2000 | Douglas et al. |
| 6,147,342 | A | 11/2000 | Kucher |
| 6,154,855 | A | 11/2000 | Norman |
| 6,155,992 | A | 12/2000 | Henning et al. |
| 6,157,442 | A | 12/2000 | Raskas |
| 6,160,449 | A | 12/2000 | Klomsdorf et al. |
| 6,162,202 | A | 12/2000 | Sicurelli et al. |
| 6,162,611 | A | 12/2000 | Heller et al. |
| 6,164,284 | A | 12/2000 | Schulman et al. |
| 6,173,160 | B1 | 1/2001 | Liimatainen |
| 6,175,752 | B1 | 1/2001 | Say et al. |
| 6,180,416 | B1 | 1/2001 | Kurnik et al. |
| 6,185,452 | B1 | 2/2001 | Schulman et al. |
| 6,186,982 | B1 | 2/2001 | Gross et al. |
| 6,192,891 | B1 | 2/2001 | Gravel et al. |
| 6,201,980 | B1 | 3/2001 | Darrow et al. |
| 6,203,288 | B1 | 3/2001 | Kottke |
| 6,206,841 | B1 | 3/2001 | Cunningham et al. |
| 6,208,894 | B1 | 3/2001 | Schulman et al. |
| 6,212,416 | B1 | 4/2001 | Ward et al. |
| 6,215,206 | B1 | 4/2001 | Chitayat |
| 6,222,514 | B1 | 4/2001 | DeLuca |
| 6,228,100 | B1 | 5/2001 | Schraga |
| 6,232,370 | B1 | 5/2001 | Kubota et al. |
| 6,233,471 | B1 | 5/2001 | Berner et al. |
| 6,233,539 | B1 | 5/2001 | Brown |
| 6,242,961 | B1 | 6/2001 | Liu et al. |
| 6,245,060 | B1 | 6/2001 | Loomis et al. |
| 6,248,067 | B1 | 6/2001 | Causey, III et al. |
| 6,262,708 | B1 | 7/2001 | Chu |
| 6,272,364 | B1 | 8/2001 | Kurnik |
| 6,278,425 | B1 | 8/2001 | DeLuca |
| 6,280,587 | B1 | 8/2001 | Matsumoto |
| 6,283,926 | B1 | 9/2001 | Cunningham et al. |
| 6,283,951 | B1 | 9/2001 | Flaherty et al. |
| 6,284,478 | B1 | 9/2001 | Heller et al. |
| 6,288,653 | B1 | 9/2001 | Shih |
| 6,293,925 | B1 | 9/2001 | Safabash et al. |
| 6,295,506 | B1 | 9/2001 | Heinonen et al. |
| 6,298,254 | B2 | 10/2001 | Tamada |
| 6,298,255 | B1 | 10/2001 | Cordero et al. |
| 6,299,578 | B1 | 10/2001 | Kurnik et al. |
| 6,301,499 | B1 | 10/2001 | Carlson et al. |
| 6,306,104 | B1 | 10/2001 | Cunningham et al. |
| 6,309,351 | B1 | 10/2001 | Kurnik et al. |
| 6,312,888 | B1 | 11/2001 | Wong et al. |
| 6,315,721 | B2 | 11/2001 | Schulman et al. |
| 6,326,160 | B1 | 12/2001 | Dunn et al. |
| 6,329,161 | B1 | 12/2001 | Heller et al. |
| 6,331,244 | B1 | 12/2001 | Lewis et al. |
| 6,338,790 | B1 | 1/2002 | Feldman et al. |
| 6,341,232 | B1 | 1/2002 | Conn et al. |
| 6,356,776 | B1 | 3/2002 | Berner et al. |
| 6,360,888 | B1 | 3/2002 | McIvor et al. |
| 6,366,793 | B1 | 4/2002 | Bell et al. |
| 6,368,141 | B1 | 4/2002 | Van Antwerp et al. |
| 6,368,274 | B1 | 4/2002 | Van Antwerp et al. |
| 6,372,371 | B1 | 4/2002 | Iarochenko et al. |
| 6,375,344 | B1 | 4/2002 | Hanson et al. |
| 6,375,638 | B2 | 4/2002 | Nason et al. |
| 6,377,894 | B1 | 4/2002 | Deweese et al. |
| 6,379,301 | B1 | 4/2002 | Worthington et al. |
| 6,381,496 | B1 | 4/2002 | Meadows et al. |
| 6,393,318 | B1 | 5/2002 | Conn et al. |
| 6,403,944 | B1 | 6/2002 | MacKenzie et al. |
| 6,405,066 | B1 | 6/2002 | Essenpreis et al. |
| 6,408,402 | B1 | 6/2002 | Norman |
| 6,417,074 | B2 | 7/2002 | Kopley et al. |
| 6,418,332 | B1 | 7/2002 | Mastrototaro et al. |
| 6,419,642 | B1 | 7/2002 | Marchitto et al. |
| 6,425,829 | B1 | 7/2002 | Julien |
| 6,427,088 | B1 | 7/2002 | Bowman, IV et al. |
| 6,432,585 | B1 | 8/2002 | Kawakami et al. |
| 6,437,379 | B2 | 8/2002 | Kopley et al. |
| 6,438,385 | B1 | 8/2002 | Heinonen et al. |
| 6,438,414 | B1 | 8/2002 | Conn et al. |
| 6,442,413 | B1 | 8/2002 | Silver |
| 6,445,374 | B2 | 9/2002 | Albert et al. |
| 6,461,329 | B1 | 10/2002 | Van Antwerp et al. |
| 6,462,162 | B2 | 10/2002 | Van Antwerp et al. |
| 6,464,848 | B1 | 10/2002 | Matsumoto |
| 6,466,807 | B1 | 10/2002 | Dobson et al. |
| 6,466,810 | B1 | 10/2002 | Ward et al. |
| 6,468,222 | B1 | 10/2002 | Mault et al. |
| 6,471,980 | B2 | 10/2002 | Sirhan et al. |
| 6,472,991 | B1 | 10/2002 | Schulman et al. |
| 6,475,196 | B1 | 11/2002 | Vachon |
| 6,478,736 | B1 | 11/2002 | Mault |
| 6,480,730 | B2 | 11/2002 | Darrow et al. |
| 6,482,158 | B2 | 11/2002 | Mault |
| 6,482,176 | B1 | 11/2002 | Wich |
| 6,484,045 | B1 | 11/2002 | Holker et al. |
| 6,484,046 | B1 | 11/2002 | Say et al. |
| 6,485,138 | B1 | 11/2002 | Kubota et al. |
| 6,485,461 | B1 | 11/2002 | Mason et al. |
| 6,485,465 | B2 | 11/2002 | Morberg et al. |
| 6,492,180 | B2 | 12/2002 | Brown et al. |
| 6,498,043 | B1 | 12/2002 | Schulman et al. |
| 6,506,168 | B1 | 1/2003 | Fathallah et al. |
| 6,513,532 | B2 | 2/2003 | Mault et al. |
| 6,514,460 | B1 | 2/2003 | Fendrock |
| 6,514,689 | B2 | 2/2003 | Han et al. |
| 6,514,718 | B2 | 2/2003 | Heller et al. |
| 6,522,530 | B2 | 2/2003 | Bang |
| 6,525,330 | B2 * | 2/2003 | Paolini et al. ............. 250/559.1 |

(56) References Cited

U.S. PATENT DOCUMENTS

| | | |
|---|---|---|
| 6,526,298 B1 | 2/2003 | Khalil et al. |
| 6,529,772 B2 | 3/2003 | Carlson et al. |
| 6,530,915 B1 | 3/2003 | Eppstein et al. |
| 6,535,753 B1 | 3/2003 | Raskas |
| 6,537,243 B1 | 3/2003 | Henning et al. |
| 6,540,675 B2 | 4/2003 | Aceti et al. |
| 6,540,891 B1 | 4/2003 | Stewart et al. |
| 6,543,224 B1 | 4/2003 | Barooah |
| 6,544,212 B2 | 4/2003 | Galley et al. |
| 6,546,269 B1 | 4/2003 | Kurnik |
| 6,549,796 B2 | 4/2003 | Sohrab |
| 6,551,276 B1 * | 4/2003 | Mann et al. ............... 604/131 |
| 6,554,798 B1 | 4/2003 | Mann et al. |
| 6,558,320 B1 | 5/2003 | Causey, III et al. |
| 6,558,321 B1 * | 5/2003 | Burd et al. ............... 600/300 |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,564,807 B1 | 5/2003 | Schulman et al. |
| 6,565,509 B1 | 5/2003 | Say et al. |
| 6,565,738 B1 | 5/2003 | Henning et al. |
| 6,569,157 B1 | 5/2003 | Shain et al. |
| 6,571,128 B2 | 5/2003 | Lebel et al. |
| 6,571,200 B1 | 5/2003 | Mault |
| 6,576,117 B1 | 6/2003 | Iketaki et al. |
| 6,577,899 B2 | 6/2003 | Lebel et al. |
| 6,579,498 B1 | 6/2003 | Eglise |
| 6,579,690 B1 | 6/2003 | Bonnecaze et al. |
| 6,582,393 B2 | 6/2003 | Sage, Jr. |
| 6,585,644 B2 | 7/2003 | Lebel et al. |
| 6,586,971 B1 | 7/2003 | Naffziger et al. |
| 6,587,705 B1 | 7/2003 | Kim et al. |
| 6,589,229 B1 | 7/2003 | Connelly et al. |
| 6,594,514 B2 | 7/2003 | Berner et al. |
| 6,595,919 B2 | 7/2003 | Berner et al. |
| 6,596,016 B1 | 7/2003 | Vreman et al. |
| 6,600,997 B2 | 7/2003 | Deweese et al. |
| 6,602,469 B1 | 8/2003 | Maus et al. |
| 6,607,509 B2 | 8/2003 | Bobroff et al. |
| 6,610,012 B2 | 8/2003 | Mault |
| 6,612,306 B1 | 9/2003 | Mault |
| 6,615,061 B1 | 9/2003 | Khalil et al. |
| 6,615,074 B2 | 9/2003 | Mickle et al. |
| 6,618,603 B2 | 9/2003 | Varalli et al. |
| 6,620,106 B2 | 9/2003 | Mault |
| 6,623,501 B2 | 9/2003 | Heller et al. |
| 6,629,934 B2 | 10/2003 | Mault et al. |
| 6,633,095 B1 | 10/2003 | Swope et al. |
| 6,633,772 B2 * | 10/2003 | Ford et al. ............... 600/345 |
| 6,635,014 B2 | 10/2003 | Starkweather et al. |
| 6,641,533 B2 | 11/2003 | Causey, III et al. |
| 6,645,142 B2 | 11/2003 | Braig et al. |
| 6,648,821 B2 | 11/2003 | Lebel et al. |
| 6,650,064 B2 | 11/2003 | Guthrie et al. |
| 6,653,091 B1 | 11/2003 | Dunn et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,980 B2 | 12/2003 | Morberg et al. |
| 6,668,196 B1 | 12/2003 | Villegas et al. |
| 6,669,663 B1 | 12/2003 | Thompson |
| 6,669,669 B2 | 12/2003 | Flaherty et al. |
| 6,670,806 B2 | 12/2003 | Wendt et al. |
| 6,679,841 B2 | 1/2004 | Bojan et al. |
| 6,687,522 B2 | 2/2004 | Tamada |
| 6,687,546 B2 | 2/2004 | Lebel et al. |
| 6,692,457 B2 | 2/2004 | Flaherty |
| 6,694,191 B2 | 2/2004 | Lebel et al. |
| 6,695,885 B2 | 2/2004 | Schulman et al. |
| 6,699,218 B2 | 3/2004 | Flaherty et al. |
| 6,702,857 B2 | 3/2004 | Brauker et al. |
| 6,723,072 B2 | 4/2004 | Flaherty et al. |
| 6,728,560 B2 * | 4/2004 | Kollias et al. ............... 600/316 |
| 6,730,200 B1 | 5/2004 | Stewart et al. |
| 6,731,976 B2 | 5/2004 | Penn et al. |
| 6,733,446 B2 | 5/2004 | Lebel et al. |
| 6,736,777 B2 | 5/2004 | Kim et al. |
| 6,736,797 B1 | 5/2004 | Larsen et al. |
| 6,738,654 B2 | 5/2004 | Sohrab |
| 6,740,059 B2 | 5/2004 | Flaherty |
| 6,740,075 B2 | 5/2004 | Lebel et al. |
| 6,741,877 B1 | 5/2004 | Shults et al. |
| 6,743,635 B2 | 6/2004 | Neel et al. |
| 6,746,582 B2 | 6/2004 | Heller et al. |
| 6,749,587 B2 | 6/2004 | Flaherty |
| 6,752,785 B2 | 6/2004 | Van Antwerp et al. |
| 6,752,787 B1 | 6/2004 | Causey, III et al. |
| 6,758,810 B2 | 7/2004 | Lebel et al. |
| 6,764,581 B1 | 7/2004 | Forrow et al. |
| 6,768,425 B2 | 7/2004 | Flaherty et al. |
| 6,770,030 B1 | 8/2004 | Schaupp et al. |
| 6,770,729 B2 | 8/2004 | Van Antwerp |
| 6,773,563 B2 | 8/2004 | Matsumoto |
| 6,779,984 B2 | 8/2004 | Lilie et al. |
| 6,789,195 B1 * | 9/2004 | Prihoda et al. ............... 713/182 |
| 6,790,178 B1 | 9/2004 | Mault et al. |
| 6,794,195 B2 | 9/2004 | Colvin, Jr. |
| 6,799,861 B2 | 10/2004 | Naghi et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,816,742 B2 | 11/2004 | Kim et al. |
| 6,818,348 B1 | 11/2004 | Venkatesan et al. |
| 6,830,558 B2 | 12/2004 | Flaherty et al. |
| 6,832,114 B1 | 12/2004 | Whitehurst et al. |
| 6,833,540 B2 | 12/2004 | MacKenzie et al. |
| 6,835,553 B2 | 12/2004 | Han et al. |
| 6,837,858 B2 | 1/2005 | Cunningham et al. |
| 6,839,596 B2 | 1/2005 | Nelson et al. |
| 6,840,912 B2 | 1/2005 | Kloepfer et al. |
| 6,849,237 B2 | 2/2005 | Housefield et al. |
| 6,850,790 B2 | 2/2005 | Berner et al. |
| 6,859,831 B1 | 2/2005 | Gelvin et al. |
| 6,862,465 B2 | 3/2005 | Shults et al. |
| 6,872,200 B2 | 3/2005 | Mann et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,893,396 B2 | 5/2005 | Schulze et al. |
| 6,895,265 B2 | 5/2005 | Silver |
| 6,898,451 B2 | 5/2005 | Wuori |
| 6,899,683 B2 | 5/2005 | Mault et al. |
| 6,899,684 B2 | 5/2005 | Mault et al. |
| 6,904,301 B2 | 6/2005 | Raskas |
| 6,907,127 B1 | 6/2005 | Kravitz et al. |
| 6,908,535 B2 | 6/2005 | Rankin et al. |
| 6,916,159 B2 | 7/2005 | Rush et al. |
| 6,918,874 B1 | 7/2005 | Hatch et al. |
| 6,922,576 B2 | 7/2005 | Raskas |
| 6,922,578 B2 | 7/2005 | Eppstein et al. |
| 6,923,764 B2 | 8/2005 | Aceti et al. |
| 6,927,749 B1 | 8/2005 | Klemm |
| 6,931,327 B2 | 8/2005 | Goode, Jr. et al. |
| 6,936,029 B2 | 8/2005 | Mann et al. |
| 6,949,816 B2 | 9/2005 | Brown et al. |
| 6,950,708 B2 | 9/2005 | Bowman, IV et al. |
| 6,952,603 B2 | 10/2005 | Gerber et al. |
| 6,955,650 B2 | 10/2005 | Mault et al. |
| 6,958,129 B2 | 10/2005 | Galen et al. |
| 6,958,705 B2 | 10/2005 | Lebel et al. |
| 6,960,192 B1 | 11/2005 | Flaherty et al. |
| 6,961,448 B2 | 11/2005 | Nichols et al. |
| 6,974,437 B2 | 12/2005 | Lebel et al. |
| 6,979,326 B2 | 12/2005 | Mann et al. |
| 6,990,366 B2 | 1/2006 | Say et al. |
| 6,990,372 B2 | 1/2006 | Perron et al. |
| 6,997,911 B2 * | 2/2006 | Klitmose ............... 604/232 |
| 6,997,920 B2 | 2/2006 | Mann et al. |
| 6,999,810 B2 | 2/2006 | Berner et al. |
| 7,003,340 B2 | 2/2006 | Say et al. |

(56) References Cited

U.S. PATENT DOCUMENTS

| | | |
|---|---|---|
| 7,003,341 B2 | 2/2006 | Say et al. |
| 7,005,857 B2 | 2/2006 | Stiene et al. |
| 7,006,858 B2 | 2/2006 | Silver et al. |
| 7,010,356 B2 | 3/2006 | Jog et al. |
| 7,011,630 B2 | 3/2006 | Desai et al. |
| 7,018,360 B2 | 3/2006 | Flaherty et al. |
| 7,020,508 B2 | 3/2006 | Stirovic et al. |
| 7,024,245 B2 | 4/2006 | Lebel et al. |
| 7,024,249 B2 | 4/2006 | Weisner et al. |
| 7,025,743 B2 | 4/2006 | Mann et al. |
| 7,029,444 B2 | 4/2006 | Shin et al. |
| 7,029,455 B2 | 4/2006 | Flaherty |
| 7,034,677 B2 | 4/2006 | Steinthal et al. |
| 7,041,468 B2 | 5/2006 | Drucker et al. |
| 7,043,287 B1 | 5/2006 | Khalil et al. |
| 7,052,251 B2 | 5/2006 | Nason et al. |
| 7,058,437 B2 | 6/2006 | Buse et al. |
| 7,067,498 B2 | 6/2006 | Wolf et al. |
| 7,070,591 B2 | 7/2006 | Adams et al. |
| 7,072,738 B2 | 7/2006 | Bonney et al. |
| 7,074,307 B2 | 7/2006 | Simpson et al. |
| 7,077,328 B2 | 7/2006 | Krishnaswamy et al. |
| 7,079,901 B1 | 7/2006 | Loftin et al. |
| 7,081,195 B2 | 7/2006 | Simpson et al. |
| 7,083,593 B2 | 8/2006 | Stultz |
| 7,086,277 B2 | 8/2006 | Tess et al. |
| 7,092,762 B1 | 8/2006 | Loftin et al. |
| 7,097,983 B2 | 8/2006 | Markovsky et al. |
| 7,098,803 B2 | 8/2006 | Mann et al. |
| 7,108,711 B2 | 9/2006 | Vogel et al. |
| 7,108,778 B2 | 9/2006 | Simpson et al. |
| 7,110,803 B2 | 9/2006 | Shults et al. |
| 7,114,502 B2 | 10/2006 | Schulman et al. |
| 7,123,206 B2 | 10/2006 | Hess et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,136,704 B2 | 11/2006 | Schulman |
| 7,137,964 B2 | 11/2006 | Flaherty |
| 7,144,384 B2 | 12/2006 | Gorman et al. |
| 7,149,581 B2 | 12/2006 | Goedeke |
| 7,153,212 B1 | 12/2006 | Karten et al. |
| 7,154,398 B2 | 12/2006 | Chen et al. |
| 7,163,511 B2 | 1/2007 | Conn et al. |
| 7,167,818 B2 | 1/2007 | Brown |
| 7,171,274 B2 | 1/2007 | Starkweather et al. |
| 7,174,199 B2 | 2/2007 | Berner et al. |
| 7,181,261 B2 | 2/2007 | Silver et al. |
| 7,186,566 B2 | 3/2007 | Qian |
| 7,186,791 B2 | 3/2007 | Bruno et al. |
| 7,192,450 B2 | 3/2007 | Brauker et al. |
| 7,193,521 B2 | 3/2007 | Morberg et al. |
| 7,198,603 B2 | 4/2007 | Penner et al. |
| 7,202,734 B1 | 4/2007 | Raab |
| 7,205,409 B2 | 4/2007 | Pei et al. |
| 7,207,974 B2 | 4/2007 | Safabash et al. |
| 7,208,119 B1 | 4/2007 | Kurtock et al. |
| 7,211,048 B1 | 5/2007 | Najafi et al. |
| 7,218,017 B1 | 5/2007 | Chitayet et al. |
| 7,225,535 B2 | 6/2007 | Feldman et al. |
| 7,226,278 B2 | 6/2007 | Nason et al. |
| 7,226,442 B2 | 6/2007 | Sheppard, Jr. et al. |
| 7,226,978 B2 | 6/2007 | Tapsak et al. |
| 7,258,666 B2 | 8/2007 | Brown |
| 7,266,400 B2 | 9/2007 | Fine et al. |
| 7,267,665 B2 | 9/2007 | Steil et al. |
| 7,276,029 B2 | 10/2007 | Goode, Jr. et al. |
| 7,283,867 B2 | 10/2007 | Strother et al. |
| 7,291,497 B2 | 11/2007 | Holmes et al. |
| 7,299,080 B2 | 11/2007 | Acosta et al. |
| 7,303,549 B2 | 12/2007 | Flaherty et al. |
| 7,310,544 B2 | 12/2007 | Brister et al. |
| 7,318,816 B2 | 1/2008 | Bobroff et al. |
| 7,323,091 B1 | 1/2008 | Gillette et al. |
| 7,324,949 B2 * | 1/2008 | Bristol ............................ 705/3 |
| 7,343,188 B2 | 3/2008 | Sohrab |
| 7,364,592 B2 | 4/2008 | Carr-Brendel et al. |
| 7,366,556 B2 | 4/2008 | Brister et al. |
| 7,371,247 B2 | 5/2008 | Boeker et al. |
| 7,379,765 B2 | 5/2008 | Petisce et al. |
| 7,424,318 B2 | 9/2008 | Brister et al. |
| 7,436,511 B2 | 10/2008 | Ruchti et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,480,138 B2 | 1/2009 | Kogan et al. |
| 7,494,465 B2 | 2/2009 | Brister et al. |
| 7,497,827 B2 | 3/2009 | Brister et al. |
| 7,510,526 B2 | 3/2009 | Merry et al. |
| 7,519,408 B2 | 4/2009 | Rasdal et al. |
| 7,583,190 B2 | 9/2009 | Reggiardo et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,613,491 B2 | 11/2009 | Boock et al. |
| 7,615,007 B2 | 11/2009 | Shults et al. |
| 7,620,437 B2 | 11/2009 | Reggiardo |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,679,407 B2 | 3/2010 | Reggiardo |
| 7,711,402 B2 | 5/2010 | Shults et al. |
| 7,713,574 B2 | 5/2010 | Brister et al. |
| 7,715,893 B2 | 5/2010 | Kamath et al. |
| 7,756,561 B2 | 7/2010 | Reggiardo et al. |
| 7,768,408 B2 | 8/2010 | Reggiardo et al. |
| 7,775,444 B2 | 8/2010 | DeRocco et al. |
| 7,778,795 B2 | 8/2010 | Fukushima et al. |
| 7,850,621 B2 | 12/2010 | Briggs et al. |
| 7,882,611 B2 | 2/2011 | Shah et al. |
| 7,899,545 B2 | 3/2011 | John |
| 7,911,010 B2 | 3/2011 | Stetter |
| 7,954,385 B2 | 6/2011 | Raisanen |
| 8,047,811 B2 | 11/2011 | Rush et al. |
| 8,192,394 B2 | 6/2012 | Estes et al. |
| 2001/0016682 A1 | 8/2001 | Berner et al. |
| 2001/0016683 A1 | 8/2001 | Darrow et al. |
| 2001/0016710 A1 | 8/2001 | Nason et al. |
| 2001/0020124 A1 | 9/2001 | Tamada |
| 2001/0023095 A1 | 9/2001 | Kopley et al. |
| 2001/0024864 A1 | 9/2001 | Kopley et al. |
| 2001/0029340 A1 | 10/2001 | Mault et al. |
| 2001/0034502 A1 | 10/2001 | Moberg et al. |
| 2001/0034617 A1 * | 10/2001 | Kimata ............................ 705/3 |
| 2001/0037060 A1 | 11/2001 | Thompson et al. |
| 2001/0037069 A1 | 11/2001 | Carlson et al. |
| 2001/0041830 A1 | 11/2001 | Varalli et al. |
| 2001/0044581 A1 | 11/2001 | Mault |
| 2001/0044588 A1 | 11/2001 | Mault |
| 2001/0049470 A1 | 12/2001 | Mault et al. |
| 2001/0053891 A1 | 12/2001 | Ackley |
| 2001/0056255 A1 | 12/2001 | Kost et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0010414 A1 | 1/2002 | Coston et al. |
| 2002/0019022 A1 | 2/2002 | Dunn et al. |
| 2002/0019612 A1 | 2/2002 | Watanabe et al. |
| 2002/0026937 A1 | 3/2002 | Mault |
| 2002/0027164 A1 | 3/2002 | Mault et al. |
| 2002/0028995 A1 | 3/2002 | Mault |
| 2002/0032374 A1 | 3/2002 | Holker et al. |
| 2002/0040208 A1 | 4/2002 | Flaherty et al. |
| 2002/0042090 A1 | 4/2002 | Heller et al. |
| 2002/0042561 A1 | 4/2002 | Schulman et al. |
| 2002/0045808 A1 | 4/2002 | Ford et al. |
| 2002/0047867 A1 | 4/2002 | Mault et al. |
| 2002/0053637 A1 | 5/2002 | Conn et al. |
| 2002/0062069 A1 | 5/2002 | Mault |
| 2002/0065682 A1 * | 5/2002 | Goldenberg ............................ 705/2 |

(56) References Cited

U.S. PATENT DOCUMENTS

| | | |
|---|---|---|
| 2002/0068858 A1 | 6/2002 | Braig et al. |
| 2002/0077765 A1 | 6/2002 | Mault |
| 2002/0077766 A1 | 6/2002 | Mault |
| 2002/0087056 A1 | 7/2002 | Aceti et al. |
| 2002/0091312 A1 | 7/2002 | Berner et al. |
| 2002/0091454 A1 | 7/2002 | Vasko |
| 2002/0103425 A1 | 8/2002 | Mault |
| 2002/0107433 A1 | 8/2002 | Mault |
| 2002/0107476 A1 | 8/2002 | Mann et al. |
| 2002/0109600 A1 | 8/2002 | Mault et al. |
| 2002/0118090 A1 | 8/2002 | Park et al. |
| 2002/0119711 A1 | 8/2002 | Van Antwerp et al. |
| 2002/0124017 A1 | 9/2002 | Mault |
| 2002/0133378 A1 | 9/2002 | Mault et al. |
| 2002/0161286 A1 | 10/2002 | Gerber et al. |
| 2002/0169394 A1 | 11/2002 | Eppstein et al. |
| 2002/0169439 A1 | 11/2002 | Flaherty et al. |
| 2002/0177764 A1 | 11/2002 | Sohrab |
| 2002/0193679 A1* | 12/2002 | Malave et al. ................ 600/407 |
| 2003/0009133 A1 | 1/2003 | Ramey |
| 2003/0023182 A1 | 1/2003 | Mault et al. |
| 2003/0023317 A1 | 1/2003 | Brauker et al. |
| 2003/0028089 A1 | 2/2003 | Galley et al. |
| 2003/0028120 A1 | 2/2003 | Mault et al. |
| 2003/0032868 A1 | 2/2003 | Graskov et al. |
| 2003/0032874 A1 | 2/2003 | Rhodes et al. |
| 2003/0040683 A1 | 2/2003 | Rule et al. |
| 2003/0050546 A1 | 3/2003 | Desai et al. |
| 2003/0050575 A1 | 3/2003 | Diermann et al. |
| 2003/0055380 A1 | 3/2003 | Flaherty et al. |
| 2003/0060692 A1 | 3/2003 | Ruchti et al. |
| 2003/0060765 A1 | 3/2003 | Campbell et al. |
| 2003/0065254 A1 | 4/2003 | Schulman et al. |
| 2003/0065257 A1 | 4/2003 | Mault et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0065308 A1 | 4/2003 | Lebel et al. |
| 2003/0078560 A1 | 4/2003 | Miller et al. |
| 2003/0100040 A1 | 5/2003 | Bonnecaze et al. |
| 2003/0100821 A1 | 5/2003 | Heller et al. |
| 2003/0105407 A1 | 6/2003 | Pearce, Jr. et al. |
| 2003/0107487 A1 | 6/2003 | Korman et al. |
| 2003/0108976 A1 | 6/2003 | Braig et al. |
| 2003/0118460 A1 | 6/2003 | Lilie et al. |
| 2003/0130616 A1 | 7/2003 | Steil et al. |
| 2003/0134347 A1 | 7/2003 | Heller et al. |
| 2003/0135100 A1 | 7/2003 | Kim et al. |
| 2003/0135333 A1 | 7/2003 | Aceti et al. |
| 2003/0153820 A1 | 8/2003 | Berner et al. |
| 2003/0153821 A1 | 8/2003 | Berner et al. |
| 2003/0154405 A1* | 8/2003 | Harrison ........................ 713/201 |
| 2003/0158472 A1 | 8/2003 | Sohrab |
| 2003/0158707 A1 | 8/2003 | Doi |
| 2003/0167035 A1 | 9/2003 | Flaherty et al. |
| 2003/0175806 A1 | 9/2003 | Rule et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0191376 A1 | 10/2003 | Samuels et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0198558 A1 | 10/2003 | Nason et al. |
| 2003/0199825 A1 | 10/2003 | Flaherty |
| 2003/0199837 A1 | 10/2003 | Vachon |
| 2003/0208110 A1 | 11/2003 | Mault et al. |
| 2003/0208113 A1 | 11/2003 | Mault et al. |
| 2003/0208133 A1 | 11/2003 | Mault |
| 2003/0208154 A1 | 11/2003 | Close et al. |
| 2003/0208409 A1 | 11/2003 | Mault |
| 2003/0212346 A1 | 11/2003 | Yuzhakov et al. |
| 2003/0212364 A1 | 11/2003 | Mann et al. |
| 2003/0212379 A1 | 11/2003 | Bylund et al. |
| 2003/0214304 A1 | 11/2003 | Karinka et al. |
| 2003/0217966 A1 | 11/2003 | Tapsak et al. |
| 2003/0225360 A1 | 12/2003 | Eppstein et al. |
| 2003/0225361 A1 | 12/2003 | Sabra |
| 2003/0226695 A1 | 12/2003 | Mault |
| 2003/0232370 A1 | 12/2003 | Trifiro |
| 2003/0235817 A1 | 12/2003 | Bartkowiak et al. |
| 2004/0010207 A1 | 1/2004 | Flaherty et al. |
| 2004/0011671 A1 | 1/2004 | Shults et al. |
| 2004/0015131 A1 | 1/2004 | Flaherty et al. |
| 2004/0018486 A1 | 1/2004 | Dunn et al. |
| 2004/0019321 A1 | 1/2004 | Sage et al. |
| 2004/0027253 A1 | 2/2004 | Marsh et al. |
| 2004/0034289 A1 | 2/2004 | Teller et al. |
| 2004/0039256 A1 | 2/2004 | Kawatahara et al. |
| 2004/0041749 A1 | 3/2004 | Dixon |
| 2004/0045879 A1 | 3/2004 | Shults et al. |
| 2004/0054263 A1* | 3/2004 | Moerman et al. .............. 600/300 |
| 2004/0059201 A1 | 3/2004 | Ginsberg |
| 2004/0059284 A1 | 3/2004 | Nash et al. |
| 2004/0064088 A1 | 4/2004 | Gorman et al. |
| 2004/0064096 A1 | 4/2004 | Flaherty et al. |
| 2004/0064133 A1 | 4/2004 | Miller et al. |
| 2004/0072357 A1 | 4/2004 | Stiene et al. |
| 2004/0073095 A1 | 4/2004 | Causey, III et al. |
| 2004/0085215 A1 | 5/2004 | Moberg et al. |
| 2004/0096959 A1 | 5/2004 | Stiene et al. |
| 2004/0100376 A1 | 5/2004 | Lye et al. |
| 2004/0106858 A1 | 6/2004 | Say et al. |
| 2004/0106859 A1 | 6/2004 | Say et al. |
| 2004/0106860 A1 | 6/2004 | Say et al. |
| 2004/0108226 A1 | 6/2004 | Polychronakos et al. |
| 2004/0115067 A1 | 6/2004 | Rush et al. |
| 2004/0116847 A1 | 6/2004 | Wall |
| 2004/0116866 A1 | 6/2004 | Gorman et al. |
| 2004/0122353 A1 | 6/2004 | Shahmirian et al. |
| 2004/0132220 A1 | 7/2004 | Fish |
| 2004/0133092 A1 | 7/2004 | Kain |
| 2004/0152622 A1 | 8/2004 | Keith et al. |
| 2004/0153032 A1 | 8/2004 | Garribotto et al. |
| 2004/0158137 A1 | 8/2004 | Eppstein et al. |
| 2004/0162473 A1 | 8/2004 | Sohrab |
| 2004/0164961 A1 | 8/2004 | Bal et al. |
| 2004/0167383 A1 | 8/2004 | Kim et al. |
| 2004/0167464 A1 | 8/2004 | Ireland et al. |
| 2004/0167801 A1 | 8/2004 | Say et al. |
| 2004/0171921 A1 | 9/2004 | Say et al. |
| 2004/0176913 A1 | 9/2004 | Kawatahara et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0199059 A1 | 10/2004 | Brauker et al. |
| 2004/0202576 A1 | 10/2004 | Aceti et al. |
| 2004/0207054 A1 | 10/2004 | Brown et al. |
| 2004/0208780 A1 | 10/2004 | Faries, Jr. et al. |
| 2004/0210184 A1 | 10/2004 | Kost et al. |
| 2004/0225338 A1 | 11/2004 | Lebel et al. |
| 2004/0236200 A1 | 11/2004 | Say et al. |
| 2004/0248204 A1 | 12/2004 | Moerman |
| 2004/0249250 A1 | 12/2004 | McGee et al. |
| 2004/0249253 A1 | 12/2004 | Racchini et al. |
| 2004/0249254 A1 | 12/2004 | Racchini et al. |
| 2004/0249999 A1 | 12/2004 | Connolly et al. |
| 2004/0253736 A1 | 12/2004 | Stout et al. |
| 2004/0254429 A1 | 12/2004 | Yang |
| 2004/0254434 A1 | 12/2004 | Goodnow et al. |
| 2004/0254884 A1 | 12/2004 | Haber et al. |
| 2004/0263354 A1 | 12/2004 | Mann et al. |
| 2004/0264396 A1 | 12/2004 | Ginzburg et al. |
| 2005/0003470 A1 | 1/2005 | Nelson et al. |
| 2005/0009126 A1 | 1/2005 | Andrews et al. |
| 2005/0010269 A1 | 1/2005 | Lebel et al. |
| 2005/0016276 A1 | 1/2005 | Guan et al. |
| 2005/0027179 A1 | 2/2005 | Berner et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |

(56) References Cited

U.S. PATENT DOCUMENTS

| | | |
|---|---|---|
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0038680 A1 | 2/2005 | McMahon |
| 2005/0043598 A1 | 2/2005 | Goode, Jr. et al. |
| 2005/0043894 A1 | 2/2005 | Fernandez |
| 2005/0045476 A1 | 3/2005 | Neel et al. |
| 2005/0049473 A1 | 3/2005 | Desai et al. |
| 2005/0051580 A1 | 3/2005 | Ramey |
| 2005/0053365 A1 | 3/2005 | Adams et al. |
| 2005/0054909 A1 | 3/2005 | Petisce et al. |
| 2005/0059926 A1 | 3/2005 | Sage, Jr. et al. |
| 2005/0065464 A1 | 3/2005 | Talbot et al. |
| 2005/0090607 A1 | 4/2005 | Tapsak et al. |
| 2005/0090808 A1 | 4/2005 | Malave et al. |
| 2005/0112169 A1 | 5/2005 | Brauker et al. |
| 2005/0113653 A1 | 5/2005 | Fox et al. |
| 2005/0113657 A1 | 5/2005 | Alarcon et al. |
| 2005/0113658 A1 | 5/2005 | Jacobson et al. |
| 2005/0118726 A1 | 6/2005 | Scultz et al. |
| 2005/0121322 A1 | 6/2005 | Say et al. |
| 2005/0124873 A1 | 6/2005 | Shults et al. |
| 2005/0137471 A1 | 6/2005 | Haar et al. |
| 2005/0143635 A1 | 6/2005 | Kamath et al. |
| 2005/0143636 A1 | 6/2005 | Zhang et al. |
| 2005/0148003 A1 | 7/2005 | Keith et al. |
| 2005/0154271 A1 | 7/2005 | Rasdal et al. |
| 2005/0161346 A1 | 7/2005 | Simpson et al. |
| 2005/0171503 A1 | 8/2005 | Van Den Berghe et al. |
| 2005/0171512 A1 | 8/2005 | Flaherty |
| 2005/0171513 A1 | 8/2005 | Mann et al. |
| 2005/0173245 A1 | 8/2005 | Feldman et al. |
| 2005/0176136 A1 | 8/2005 | Burd et al. |
| 2005/0177036 A1 | 8/2005 | Shults et al. |
| 2005/0181012 A1 | 8/2005 | Saint et al. |
| 2005/0182306 A1 | 8/2005 | Sloan |
| 2005/0182358 A1 | 8/2005 | Veit et al. |
| 2005/0182366 A1 | 8/2005 | Vogt et al. |
| 2005/0182451 A1 | 8/2005 | Griffin et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0203461 A1 | 9/2005 | Flaherty et al. |
| 2005/0214892 A1 | 9/2005 | Kovatchev et al. |
| 2005/0215871 A1 | 9/2005 | Feldman et al. |
| 2005/0215872 A1 | 9/2005 | Berner et al. |
| 2005/0218880 A1 | 10/2005 | Ioffe |
| 2005/0235732 A1 | 10/2005 | Rush |
| 2005/0236361 A1 | 10/2005 | Ufer et al. |
| 2005/0238503 A1 | 10/2005 | Rush et al. |
| 2005/0238507 A1 | 10/2005 | DiIanni et al. |
| 2005/0239154 A1 | 10/2005 | Feldman et al. |
| 2005/0239518 A1 | 10/2005 | D'Agostino et al. |
| 2005/0245795 A1 | 11/2005 | Goode, Jr. et al. |
| 2005/0245799 A1 | 11/2005 | Brauker et al. |
| 2005/0249506 A1 | 11/2005 | Fuse |
| 2005/0249606 A1 | 11/2005 | Rush |
| 2005/0251083 A1 | 11/2005 | Carr-Brendel et al. |
| 2005/0261660 A1 | 11/2005 | Choi |
| 2005/0267550 A1 | 12/2005 | Hess et al. |
| 2005/0267780 A1 | 12/2005 | Ray et al. |
| 2005/0271546 A1 | 12/2005 | Gerber et al. |
| 2005/0271547 A1 | 12/2005 | Gerber et al. |
| 2005/0272640 A1 | 12/2005 | Doyle, III et al. |
| 2005/0272985 A1 | 12/2005 | Kotulla et al. |
| 2005/0277844 A1 | 12/2005 | Strother et al. |
| 2005/0287620 A1 | 12/2005 | Heller et al. |
| 2006/0001538 A1 | 1/2006 | Kraft et al. |
| 2006/0001550 A1 | 1/2006 | Mann et al. |
| 2006/0001551 A1 | 1/2006 | Kraft et al. |
| 2006/0003398 A1 | 1/2006 | Heller et al. |
| 2006/0004271 A1 | 1/2006 | Peyser et al. |
| 2006/0004603 A1 | 1/2006 | Peterka et al. |
| 2006/0007017 A1 | 1/2006 | Mann et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025663 A1 | 2/2006 | Talbot et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0036187 A1 | 2/2006 | Vos et al. |
| 2006/0040402 A1 | 2/2006 | Brauker et al. |
| 2006/0041229 A1 | 2/2006 | Garibotto et al. |
| 2006/0052679 A1 | 3/2006 | Kotulla et al. |
| 2006/0058602 A1 | 3/2006 | Kwiatkowski et al. |
| 2006/0058627 A1 | 3/2006 | Flaherty et al. |
| 2006/0063218 A1 | 3/2006 | Bartowiak et al. |
| 2006/0074564 A1 | 4/2006 | Bartkowiak et al. |
| 2006/0094986 A1 | 5/2006 | Neel et al. |
| 2006/0154642 A1 | 7/2006 | Scannell |
| 2006/0161078 A1 | 7/2006 | Schraga |
| 2006/0166629 A1 | 7/2006 | Reggiardo |
| 2006/0173259 A1 | 8/2006 | Flaherty et al. |
| 2006/0173444 A1 | 8/2006 | Choy et al. |
| 2006/0173712 A1 | 8/2006 | Joubert |
| 2006/0178633 A1 | 8/2006 | Garibotto et al. |
| 2006/0222566 A1 | 10/2006 | Brauker et al. |
| 2006/0224141 A1 | 10/2006 | Rush et al. |
| 2006/0240403 A1 | 10/2006 | List et al. |
| 2006/0247508 A1 | 11/2006 | Fennell |
| 2006/0253085 A1 | 11/2006 | Geismar et al. |
| 2006/0253086 A1 | 11/2006 | Moberg et al. |
| 2006/0273759 A1 | 12/2006 | Reggiardo |
| 2006/0282290 A1 | 12/2006 | Flaherty et al. |
| 2006/0293577 A1 | 12/2006 | Morrison et al. |
| 2007/0007133 A1 | 1/2007 | Mang et al. |
| 2007/0016381 A1 | 1/2007 | Kamath et al. |
| 2007/0032717 A1 | 2/2007 | Brister et al. |
| 2007/0078323 A1 | 4/2007 | Reggiardo et al. |
| 2007/0078818 A1 | 4/2007 | Zvitz et al. |
| 2007/0100222 A1 | 5/2007 | Mastrototaro et al. |
| 2007/0106135 A1 | 5/2007 | Sloan |
| 2007/0118405 A1 | 5/2007 | Campbell et al. |
| 2007/0135697 A1 | 6/2007 | Reggiardo |
| 2007/0153705 A1 | 7/2007 | Rosar et al. |
| 2007/0156094 A1 | 7/2007 | Safabash et al. |
| 2007/0163880 A1 | 7/2007 | Woo et al. |
| 2007/0173711 A1 | 7/2007 | Shah et al. |
| 2007/0176867 A1 | 8/2007 | Reggiardo et al. |
| 2007/0203966 A1 | 8/2007 | Brauker et al. |
| 2007/0219480 A1 | 9/2007 | Kamen et al. |
| 2007/0219597 A1 | 9/2007 | Kamen et al. |
| 2007/0235331 A1 | 10/2007 | Simpson et al. |
| 2008/0021666 A1 | 1/2008 | Goode, Jr. et al. |
| 2008/0033254 A1 | 2/2008 | Kamath et al. |
| 2008/0045824 A1 | 2/2008 | Tapsak et al. |
| 2008/0057484 A1 | 3/2008 | Miyata et al. |
| 2008/0058626 A1 | 3/2008 | Miyata et al. |
| 2008/0058678 A1 | 3/2008 | Miyata et al. |
| 2008/0058773 A1 | 3/2008 | John |
| 2008/0061961 A1 | 3/2008 | John |
| 2008/0064941 A1 | 3/2008 | Funderburk et al. |
| 2008/0071156 A1 | 3/2008 | Brister et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |

(56) References Cited

U.S. PATENT DOCUMENTS

| | | |
|---|---|---|
| 2008/0086044 A1 | 4/2008 | Brister et al. |
| 2008/0086273 A1 | 4/2008 | Shults et al. |
| 2008/0097918 A1* | 4/2008 | Spector et al. .................. 705/51 |
| 2008/0108942 A1 | 5/2008 | Brister et al. |
| 2008/0119703 A1 | 5/2008 | Brister et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0189051 A1 | 8/2008 | Goode et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200838 A1 | 8/2008 | Goldberger et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0242961 A1 | 10/2008 | Brister et al. |
| 2008/0262469 A1 | 10/2008 | Brister et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0012379 A1 | 1/2009 | Goode et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0063196 A1* | 3/2009 | Frederickson .................... 705/3 |
| 2009/0063402 A1 | 3/2009 | Hayter |
| 2009/0068954 A1 | 3/2009 | Reggiardo et al. |
| 2009/0069750 A1 | 3/2009 | Schraga |
| 2009/0076356 A1 | 3/2009 | Simpson et al. |
| 2009/0076358 A1 | 3/2009 | Reggiardo et al. |
| 2009/0076360 A1 | 3/2009 | Brister et al. |
| 2009/0076361 A1 | 3/2009 | Kamath et al. |
| 2009/0083003 A1 | 3/2009 | Reggiardo |
| 2009/0099436 A1 | 4/2009 | Brister et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0216553 A1* | 8/2009 | Cellura ............................ 705/2 |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |
| 2010/0241447 A1* | 9/2010 | Siniaguine et al. ............... 705/2 |

FOREIGN PATENT DOCUMENTS

| | | |
|---|---|---|
| EP | 0465708 | 1/1992 |
| EP | 0518524 | 12/1992 |
| EP | 0709573 | 5/1996 |
| EP | 0878707 | 11/1998 |
| EP | 0543916 | 7/2001 |
| EP | 1130638 | 9/2001 |
| EP | 0980688 | 12/2002 |
| EP | 1077634 | 7/2003 |
| EP | 1755443 | 11/2005 |
| EP | 1783536 | 5/2007 |
| EP | 1681992 | 4/2010 |
| EP | 1448489 | 8/2010 |
| EP | 2201969 | 3/2011 |
| FR | 2718492 | 10/1995 |
| JP | 1-080775 | 3/1989 |
| JP | 2001-177423 | 6/2001 |
| JP | 2001-056673 | 11/2001 |
| WO | WO-96/14026 | 5/1996 |
| WO | WO-96/34637 | 11/1996 |
| WO | WO-98/04902 | 2/1998 |

(56) References Cited

FOREIGN PATENT DOCUMENTS

| WO | WO-99/22236 | 5/1999 |
|---|---|---|
| WO | WO-99/56613 | 11/1999 |
| WO | WO-00/74753 | 12/2000 |
| WO | WO-01/41849 | 6/2001 |
| WO | WO-01/52727 | 7/2001 |
| WO | WO-01/54753 | 8/2001 |
| WO | WO-01/71186 | 9/2001 |
| WO | WO-02/39086 | 5/2002 |
| WO | WO-02/057627 | 7/2002 |
| WO | WO-02/084860 | 10/2002 |
| WO | WO-02/100263 | 12/2002 |
| WO | WO-02/100469 | 12/2002 |
| WO | WO-03/006091 | 1/2003 |
| WO | WO-03/090509 | 4/2003 |
| WO | WO-03/053503 | 7/2003 |
| WO | WO-03/071930 | 9/2003 |
| WO | WO-03/103763 | 12/2003 |
| WO | WO-2004/028337 | 4/2004 |
| WO | WO-2004/032994 | 4/2004 |
| WO | WO-2004/061420 | 7/2004 |
| WO | WO-2005/089103 | 9/2005 |
| WO | WO-2005/101994 | 11/2005 |
| WO | WO-2006/003919 | 1/2006 |
| WO | WO-2006/079114 | 7/2006 |
| WO | WO-2006/086701 | 8/2006 |
| WO | WO-2006/102412 | 9/2006 |
| WO | WO-2006/110913 | 10/2006 |
| WO | WO-2006/113408 | 10/2006 |
| WO | WO-2006/113521 | 10/2006 |
| WO | WO-2006/118947 | 11/2006 |
| WO | WO-2006/132884 | 12/2006 |
| WO | WO-2007/041072 | 4/2007 |
| WO | WO-2007/090037 | 8/2007 |
| WO | WO-2008/086541 | 7/2008 |
| WO | WO-2008/110267 | 9/2008 |

OTHER PUBLICATIONS

Barbosa, R. M., et al., "Electrochemical Studies of Zinc in Zinc-Insulin Solution", *Journal of the Royal Society of Chemistry, Analyst*, vol. 121, No. 12, 1996, pp. 1789-1793.

Bard, A. J., et al., "Methods Involving Forced Convection—Hydrodynamic Methods", *Electrochemical Methods—Fundamentals and Applications*, 2001, pp. 331-367.

Kissinger, P. T., "Introduction to Analog Instrumentation", *Laboratory Techniques in Electroanalytical Chemistry, Second Edition, Revised and Expanded*, 1996, pp. 165-194.

Ursino, M, et al., "A Mathematical Model of Cerebral Blood Flow Chemical Regulation—Part I: Diffusion Processes", *IEEE Transactions on Biomedical Engineering*, vol. 36, No. 2, 1989, pp. 183-191.

International Search Report and Written Opinion of the International Searching Authority for PCT Application No. PCT/US2007/082413 filed Oct. 24, 2007 to Abbott Diabetes Care, Inc. mailed May 2, 2008.

International Preliminary Report on Patentability and Written Opinion of the International Searching Authority for PCT Application No. PCT/US2007/082413 filed Oct. 24, 2007, mailed May 14, 2009.

European Patent Application No. EP-07854392.3, Extended European Search Report mailed Jan. 27, 2010.

Russian Patent Application No. 2009120566, English Translation & Original Language of Office Action mailed Mar. 15, 2011.

U.S. Appl. No. 11/555,187, Advisory Action mailed Feb. 23, 2010.

U.S. Appl. No. 11/555,187, Office Action mailed Mar. 23, 2009.

U.S. Appl. No. 11/555,187, Office Action mailed Oct. 13, 2009.

U.S. Appl. No. 11/555,192, Advisory Action Feb. 25, 2010.

U.S. Appl. No. 11/555,192, Office Action mailed Apr. 14, 2009.

U.S. Appl. No. 11/555,192, Office Action mailed Oct. 13, 2009.

Abstract of Japanese Publication No. JP-2001-077423, Published Mar. 23, 2001.

Chinese Patent Application No. 200780040713.9, English Translation of First Office Action mailed Feb. 23, 2011.

Japanese Patent Application No. 2009-535399, English Translation & Original Language of Office Action mailed Feb. 1, 2011.

PCT Application No. PCT/US2007/082413, International Preliminary Report on Patentability and Written Opinion of the International Searching Authority mailed May 2, 2008.

Australian Patent Application No. 2007313880, Examiner's Report mailed May 8, 2012.

Chinese Patent Application No. 200780040713.9, Original Language & English Translation of Office Action mailed Mar. 12, 2012.

Russian Patent Application No. 2009120566, Original Language & English Translation of Office Action mailed Nov. 18, 2011.

\* cited by examiner

INFUSION DEVICES AND METHODS

BACKGROUND OF THE INVENTION

A variety of medical devices are employed to monitor a health condition. For example, devices include those designed to enable a user to manage a health condition based at least in part on the level of analyte in the body. These types of devices include analyte determination devices, drug delivery devices, and the like.

Such analyte devices have become widely used in recent years for people with diabetes. Diabetics have typically measured their blood glucose level by lancing a finger tip or other body location (i.e., alternate site) to draw blood, applying the blood to a disposable test strip in a hand-held meter and allowing the meter and strip to perform an electrochemical test of the blood to determine the current glucose concentration. Such discrete or individual, in vitro tests are typically conducted at least several times per day. Detailed descriptions of such glucose monitoring systems and their use are provided in U.S. Pat. No. 7,058,437, issued to TheraSense, Inc., on Jun. 6, 2006, which is incorporated by reference herein in its entirety.

In vivo glucose monitoring devices are designed to provide continuous glucose monitoring. Some of these continuous systems employ a disposable, transcutaneous sensor that is inserted into the skin to measure glucose concentrations in interstitial fluid. A portion of the sensor protrudes from the skin and is coupled with a durable controller and transmitter unit that is attached to the skin with adhesive. A wireless handheld unit is used in combination with the skin-mounted transmitter and sensor to receive glucose readings periodically, such as once a minute. At a predetermined time interval, such as every three, five or seven days, the disposable sensor is removed and replaced with a fresh sensor which is again coupled to the reusable controller and transmitter unit. With this arrangement, a person with diabetes may continuously monitor their glucose level with the handheld unit. The handheld unit of the in vivo system can also include an in vitro test strip meter for conducting individual tests as described above. The in vitro test strip meter can be used to calibrate the continuous monitoring system each time a new in vivo sensor is implanted. Additionally, the in vitro test strip meter can be used as back up in case the in vivo system fails, a new sensor is equilibrating, or when the transmitter must be turned off, such as during takeoffs and landings when aboard an airliner. Detailed descriptions of such a continuous glucose monitoring system and its use are provided in U.S. Pat. No. 6,175,752, which is incorporated by reference herein in its entirety.

Drug delivery devices, including wholly implantable infusion pumps and pumps that infuse drug through a transcutaneously placed fluid channel such as flexible tubing, are devices that enable the controllable administration of a drug to a user. Pumps may be under the control or semi-control of a healthcare monitoring device or may be controlled by the user. Examples of such include insulin pumps used by diabetics to administer insulin for glucose control.

The purpose of in vitro or in vivo glucose monitoring, and insulin delivery devices, is to assist people with diabetes in keeping their blood glucose within a predetermined range. If a person's blood glucose level rises too high, hyperglycemia can occur. The short term effects of hyperglycemia can include fatigue, loss of cognitive ability, mood swings, excessive urination, excessive thirst and excessive hunger. Of more immediate concern, if a person's blood glucose level drops too low, hypoglycemia can occur. Like hyperglycemia, symptoms of hypoglycemia also include fatigue and loss of cognitive ability. If unchecked, however, hypoglycemia can quickly lead to loss of consciousness or coma. Some diabetics have little or no symptoms of hypoglycemia, or find it difficult to distinguish between symptoms of hyperglycemia and hypoglycemia. Long term effects of not keeping blood glucose levels within a proper range include health complications such as cardiovascular disease, chronic renal failure, retinal damage which can lead to blindness, nerve damage, impotence, and gangrene with risk of amputation of toes, feet, and even legs. Clearly, proper glucose monitoring and corrective action based on the monitoring is essential for people with diabetes to maintain their health.

Also of importance is compliance to a glucose monitoring regime. Compliance may be particularly difficult with persons who require supervision, e.g., young children or mentally impaired individuals. Compliance may include strict adherence to healthcare provider and/or caregiver provider instructions. If healthcare instructions change, it is necessary that the user be timely notified of such changes. Likewise, it is important that instructions be readily available in case a person needs to be reminded thereof.

SUMMARY OF THE INVENTION

Before summarizing the invention, it is to be understood that the invention is applicable to in vitro analyte monitoring devices, in vivo analyte monitoring devices, and a drug infusion devices. Unless otherwise indicated, specific reference herein to only one of such devices is only for the sake of brevity and not intended to limit the scope of the invention. Furthermore, the subject invention is described primarily with respect to glucose monitoring devices and insulin infusion pumps, where such descriptions are not intended to limit the scope of the invention. It is to be understood that the subject invention is applicable to any suitable analyte monitoring device and drug infusion device.

According to aspects of some embodiments of the present invention, a medical device (in vitro analyte monitoring device, in vivo analyte monitoring device, drug infusion device) is provided with alert features. These alert features assist a user in maintaining proper analyte levels. Blood glucose is one of many analytes that may be maintained using aspects of the present invention. For each user, an ideal or target analyte range can be established. Above and below this ideal range, upper and lower ranges of moderate concerns, respectively, can also be established. Above the upper range of moderate concern, an upper range of high concern can be established. Similarly, below the lower range of moderate concern, a lower range of high concern can also be established. By way of example, a user can make in vitro blood glucose measurements, such as with a handheld meter and test strip. In some embodiments of the invention, the user can be alerted by the test meter when a measurement falls within either of the upper or lower ranges of moderate concern. The alert may indicate to the user which of the upper and lower ranges of moderate concern the measurement falls into.

According to other aspects of the invention, a medical device (in vitro analyte monitoring device, in vivo analyte monitoring device, drug infusion device) is provided with alarm features. These alarm features also assist a user in maintaining a proper analyte (e.g., blood glucose) level. As described above, upper and lower blood glucose ranges of high concern can be established. In some embodiments of the invention, a test meter can be provided with alarms that warn the user when a measurement falls within either of the upper or lower ranges of high concern. Preferably, the alarm indicates to the user which of the upper and lower ranges of high concern the measurement falls into. Additionally, it is preferable that the alarms indicate a higher level of urgency than do the previously described alerts. Note that a user's analyte level may pass from an ideal range, through a range of moderate concern and into a range of high concern before the user conducts an analyte measurement. In such cases, the user may be provided with an alarm without receiving an alert first.

According to other aspects of the invention, an analyte monitoring system is provided with reminder features. The reminder features also assist a user in maintaining a proper analyte (e.g., glucose) level. Analyte ranges of moderate or high concern can be established, as described above. In some embodiments of the invention, a test meter can have a reminder feature that is triggered when a measurement value falls into a range of moderate or high concern. The reminder can prompt the user after a predetermined period of time to take another analyte measurement to ensure that the analyte level is heading toward or has returned to the ideal range. Such a reminder feature can be particularly helpful since it frees the user from either trying to remember when to retest or from setting an external alarm, if available. For those users that require supervision, such as children, the reminder feature automatically assists the caregiver by providing the user with a retest reminder, even when the care giver is not present to perform the task of reminding.

According to various aspects of the invention, the above-described alerts, alarms and reminders can be conveyed to the user visually, such as with a graphical user interface (GUI) or light emitting diode(s)(LED). In one embodiment of the invention, a fixed-segment liquid crystal display (LCD) is used as the GUI, with the value of the analyte measurement appearing in flashing numerals when not in the ideal range. In addition, or in an alternative embodiment, up and down arrow icons can be provided to display when an analyte measurement is in the upper or lower range of moderate and/or high concern. For example, a solid arrow icon can be displayed when the level is in the range of moderate concern, and a flashing arrow can be displayed when the level is in the range of high concern. Different icons can be used depending on whether the level is in the range of moderate or high concern. For instance, an arrow icon having a first size can be displayed when the analyte level is in the range of moderate concern, and a larger or vertically displaced arrow icon can be displayed when the level is in the range of high concern. Alternatively, a horizontal arrow can be displayed when the analyte level is in the ideal range, an arrow inclined upward or downward can be displayed when the level is in the upper or lower range of moderate concern, respectively, and an arrow inclined at a steeper upward or downward angle can be displayed when the level is in the upper or lower range of high concern, respectively. Alternatively, the opposite directions of the above arrows can be used to be indicative of the course of action to be taken rather than whether the current level is high or low. For instance, a high analyte level may display a downward pointed arrow to indicate that the user should lower his or her analyte level. In other embodiments, symbols such as +, − and = can be used to indicate high, low and on track readings, respectively. The use of a dot matrix display instead of or in combination with a fixed element display may be employed, e.g., to allow for more flexibility in providing alerts and/or alarms and/or reminders to a user. Text may be shown on the display, with or without accompanying icons, and with or without user feedback, to provide information to the user about a particular alert, alarm and/or reminder. For example, after a test result falling into a range of concern, text may appear explaining the significance of the results, proposing one or more courses of action, and/or indicating that the user should re-test after a certain period of time. After such a period of time has elapsed, a further text message may appear which may include instructions to conduct further tests. Some text messages may be downloaded or otherwise activated as part of a prescription from a Health Care Provider.

To reduce size and/or cost of a meter, one or more LEDs may be used to convey an alert, alarm or reminder to a user. For instance, a single LED can be illuminated when the analyte measurement is not in the ideal range. The LED can be solid when in the range of moderate concern, and flashing when in the range of high concern. Different colors in one or more LEDs can indicate different ranges. For instance green can indicate the analyte level is in the ideal range, yellow can indicate the level is in a range of moderate concern and red can indicate the level is in a range of high concern. Two LEDs can be used to indicate whether the value is high or low (or whether the user's analyte level should be raised or lowered). Three LEDs can be used, for instance with a first LED indicating an analyte level below the ideal range, a second LED indicating a level in the ideal range, and a third LED indicating a level above the ideal range. Four LEDs can be used to indicate an analyte level in the lower range of high concern, the lower range of moderate concern, the upper range of moderate concern and the upper range of high concern, respectively. A fifth LED can be added to indicate a level in the ideal range.

In addition to or instead of visual indicators of alerts, alarms and reminders, a glucometer constructed according to aspects of the present invention can incorporate audible or physical feedback. Since diabetes can adversely affect a person's eyesight, such forms of user interface can become necessary. In one embodiment of the invention, a meter can emit an audible tone to indicate an analyte reading that is outside of the ideal range. A high tone can be used to indicate a reading that is above the ideal range while a low tone can be used to indicate a reading that is below. A pulsing or intermittent tone can be used to indicate a reading that is in a range of high concern. A varying number of pulses and other variations can be employed to indicate what range the analyte reading is in. Similarly, a vibratory signal, such as used in cell phones, can be used with different variations for indicating alerts, alarms and reminders to a user.

According to various aspects of the invention, the above-described alerts, alarms and reminders can be set with default parameters during manufacture, and/or may be settable by a HCP (Health Care Professional such as a Doctor or Certified Diabetes Educator) with levels corresponding to prescribed values for a user, and/or may be user configurable. In one embodiment of the invention, a meter is provided that is set to automatically remind the user to retest after a predetermined period of time, which may be preset or configured, after a test that falls outside of an ideal analyte range. The meter may be configured to allow the user or healthcare professional to disable this feature. In an alternative embodiment, the meter is provided "out of the box" with such a reminder feature disabled, but with provisions to allow the user or healthcare professional to enable it and/or set configuration parameters. A meter can be provided that allows different reminder parameters depending on whether the underlying analyte measurement is in a range of moderate concern or a range of high concern. In one embodiment, the medical device reminds the user with a first audible signal to retest a first time period (e.g. about 30 minutes) after a test result falling in a range of moderate concern, and reminds the user with a second audible signal to retest after a second time period (e.g. about 15 minutes) after a test result falling in a range of high concern. In certain embodiments, the second audible signal has a higher volume level and/or longer duration than the first audible signal, and the second time period may be shorter than the first time period. In this embodiment, the second audible signal can also be accompanied with a vibratory signal. In this or alternative embodiments, the first and/or second signals can continue or repeat if not acknowledged by the user, such as with the push of a button, or with an actual test being conducted. The parameters of the reminders can also be different based on whether the analyte reading is above or below the ideal range, and/or can vary depending on the actual value of the analyte measurement. For each reminder (alert or alarm) the settings may include, but are not limited to, the analyte value, time to reminder, type of reminder (e.g. visual, audible, vibratory, or a combination thereof), persistence of the reminder (e.g. once, once a minute for n times, or once a minute until acknowledged), and the number of times (n) a persistent reminder will repeat.

According to certain embodiments, a medical device can be provided with alert, alarm and reminder settings, or other healthcare information that can be configured and locked by an authorized individual such as an individual in a supervisory role, e.g., a HCP or caregiver. The information may be locked until an access code is supplied, such as by an authorized individual, e.g., a HCP or a caregiver. Such an arrangement prevents those under the care of a HCP from changing a prescription or those receiving guidance from a caregiver, for instance children, from modifying configuration values. This prevents intentional or unintentional changes to the configuration values. It also prevents the bypassing of alerts, alarms or reminders, such as when a user wants to engage in behavior that may affect analyte levels, e.g., eat improperly. According to other aspects, configuration settings may be set through a medical device data port, such as when the medical device is connected to a computer for the uploading and/or downloading of information. In certain embodiments, a medical device may be configured to enable a limited number of individuals, e.g., HCP and/or a caregiver, to set and lock configuration values through the data port.

Application of the inventive aspects described herein is not limited to blood glucose monitoring and/or insulin infusion. For example, analytes may be monitored in other substances such as interstitial fluid. Moreover, monitoring of analytes other than glucose, such as lactate, acetyl choline, amylase, bilirubin, cholesterol, chorionic gonadotropin, creatine kinase (e.g., CK-MB), creatine, DNA, fructosamine, glucose, glutamine, growth hormones, hematocrit, hemoglobin (e.g. HbAlc), hormones, ketones, lactate, oxygen, peroxide, prostate-specific antigen, prothrombin, RNA, thyroid stimulating hormone, and troponin, in samples of body fluid. Meters may also be configured to determine the concentration of drugs, such as, for example, antibiotics (e.g., gentamicin, vancomycin, and the like), digitoxin, digoxin, drugs of abuse, theophylline, warfarin and the like. Such analytes can be monitored in blood, interstitial fluid, saliva, urine and other bodily fluids. It should also be noted that fewer or additional analyte measurement ranges from those described herein can be used. This includes not using ranges at all, but instead using, e.g., absolute values, formulas, lookup tables or similar concepts known to those skilled in the art to determine if or what type of alert, alarm, reminder or other indication should be made to the user for a particular analyte measurement result.

BRIEF DESCRIPTION OF THE DRAWINGS

Each of the figures diagrammatically illustrates aspects of the invention. Of these.

Variation of the invention from that shown in the figures is contemplated.

DETAILED DESCRIPTION

The following description focuses on one variation of the present invention. The variation of the invention is to be taken as a non-limiting example. It is to be understood that the invention is not limited to particular variation(s) set forth and may, of course, vary. Changes may be made to the invention described and equivalents may be substituted (both presently known and future-developed) without departing from the true spirit and scope of the invention. In addition, modifications may be made to adapt a particular situation, material, composition of matter, process, process act(s) or step(s) to the objective(s), spirit or scope of the present invention.

Figure 1:
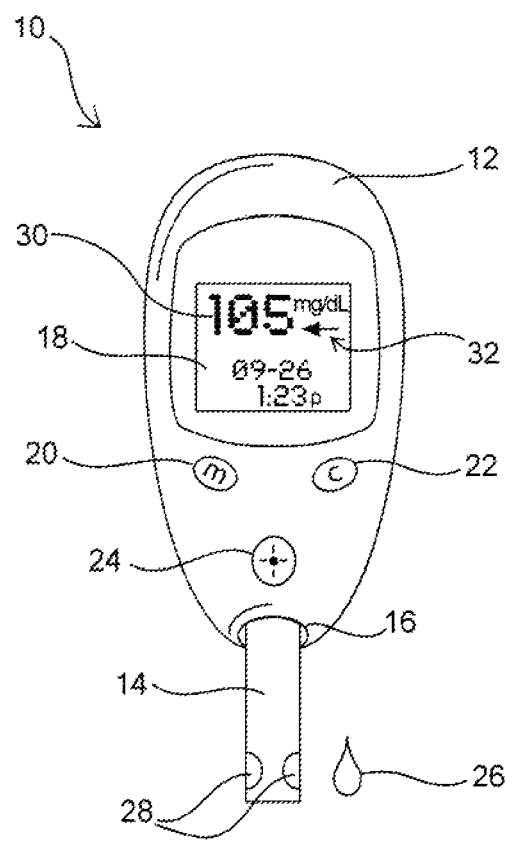
FIG. 1 is plan view showing an exemplary embodiment of an analyte monitoring system, such as a glucometer system, constructed according to aspects of the present invention.

FIG. 1 shows a top view of an exemplary analyte medical system 10, e.g., a glucometer system in this particular embodiment. Analyte medical device 10 may be an electrochemical or optical system. System 10 includes a handheld meter 12 and disposable test strip 14. Test strip 14 can be inserted into or removed from test strip port 16 of meter 12 for physical and electrical interconnection therewith. Meter 12 includes an LCD display 18 for displaying information to the meter user, and buttons 20, 22 and 24 for receiving input from the user.

In general, to take a blood glucose measurement with meter 12, a user inserts a new test strip 14 into port 16 of meter 12. Either before of after strip insertion into the meter, a user then lances a fingertip or other part of the body (i.e. alternate site) to draw a small drop of blood 26 to the surface of the skin. The meter and strip are positioned over the drop of blood 26 so that one of the sample chamber ends 28 is touching the drop of blood 26. While this particular example teaches the use of a side-fill strip, it should be noted that an end-fill, top-fill or other type of test strip may be utilized. Moreover, the analyte testing need not use a test strip at all. For instance, certain test meters may utilize a rotary test wheel for making multiple measurements, rather than individual test strips. In the present example, surface tension (wicking) automatically draws a small amount of blood 26 into the sample chamber and an electrochemical test is automatically performed by meter 12 to determine the glucose concentration in the blood 26. The glucose level 30 is then displayed on meter 12. As noted above, the subject invention is also applicable to continuous analyte monitoring systems and drug infusion devices.

The present invention may also find use with infusion systems for infusing an agent to a user such as drug infusion systems, e.g., insulin infusion systems. Such infusion systems may be wholly implantable systems or external systems. External infusion devices are typically connected to an infusion set which includes a cannula that is placed transcutaneously through the skin of the patient to infuse a select dosage of an agent. For example, external insulin infusion devices are typically connected to an infusion set which includes a cannula that is placed transcutaneously through the skin of the patient to infuse a select dosage of insulin based on the infusion device's programmed basal rates or any other infusion rates as prescribed by the patient's HCP. A user may be able to control the insulin pump device to administer additional doses of insulin during the course of wearing and operating the infusion device such as for, administering a carbohydrate bolus prior to a meal. Certain infusion devices may include a food database that has associated therewith, an amount of carbohydrate, so that the patient may better estimate the level of insulin dosage needed for, for example, calculating a bolus amount.

Figure 2:
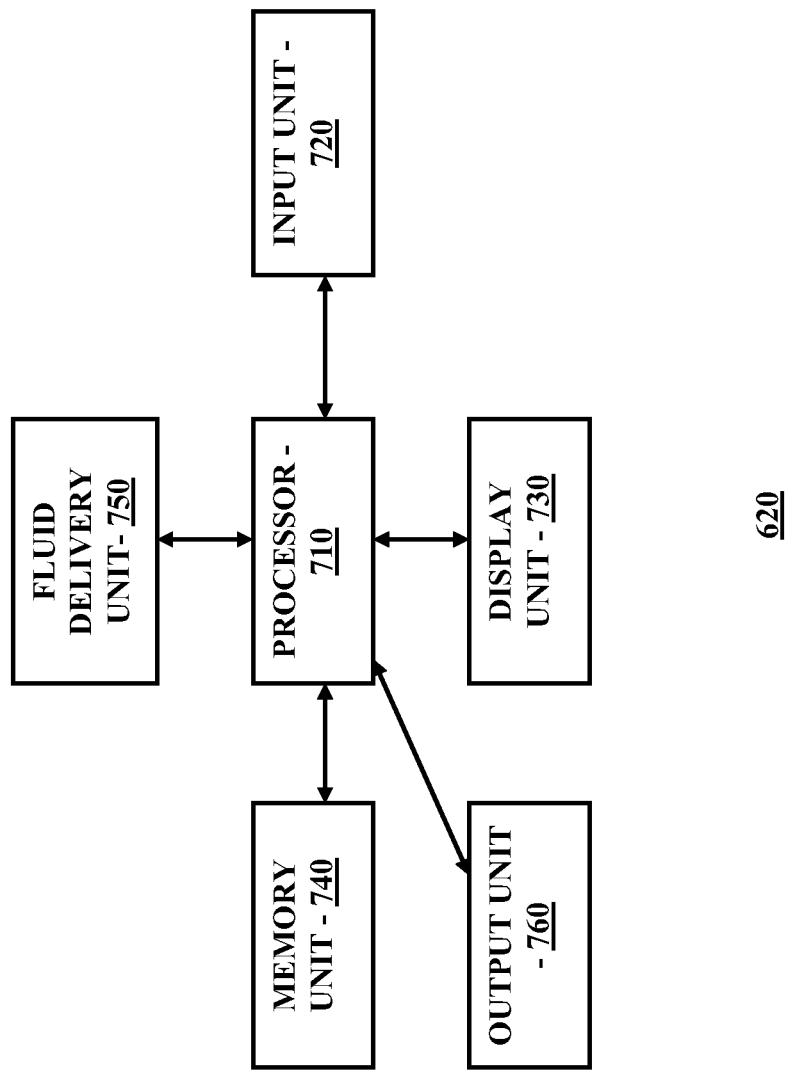
FIG. 2 is a block diagram of an exemplary embodiment of an insulin delivery device.

FIG. 2 is a block diagram of an exemplary embodiment of an insulin delivery for use with the present invention. Insulin delivery device 620 in one embodiment includes a processor 710 operatively coupled to a memory unit 740, an input unit 720, a display unit 730, an output unit 760, and a fluid delivery unit 750. In one embodiment, the processor 710 includes a microprocessor that is configured to and capable of controlling the functions of the insulin delivery device 620 by controlling and/or accessing each of the various components of the insulin delivery device 620. In one embodiment, multiple processors may be provided as safety measure and to provide redundancy in case of a single processor failure. Moreover, processing capabilities may be shared between multiple processor units within the insulin delivery device 620 such that pump functions and/or control may be performed faster and more accurately.

Input unit 720 operatively coupled to the processor 710 may include a jog dial, a key pad buttons, a touch pad screen, or any other suitable input mechanism for providing input commands to the insulin delivery device 620. More specifically, in case of a jog dial input device, or a touch pad screen, for example, the patient or user of the insulin delivery device 620 may manipulate the respective jog dial or touch pad in conjunction with the display unit 730 which performs as both a data input and output unit. The display unit 730 may include a touch sensitive screen, an LCD screen, or any other types of suitable display unit for the insulin delivery device 620 that is configured to display alphanumeric data as well as pictorial information such as icons associated with one or more predefined states of the insulin delivery device 620, or graphical representation of data such as trend charts and graphs associated with the insulin infusion rates, trend data of monitored glucose levels over a period of time, or textual notification to the patients.

Output unit 760 operatively coupled to the processor 710 may include an audible alarm including one or more tones and/or preprogrammed or programmable tunes or audio clips, or vibratory alert features having one or more pre-programmed or programmable vibratory alert levels. In one embodiment, the vibratory alert may also assist in priming the infusion tubing to minimize the potential for air or other undesirable material in the infusion tubing. Also shown is the fluid delivery unit 750 which is operatively coupled to the processor 710 and configured to deliver the insulin doses or amounts to the patient from the insulin reservoir or any other types of suitable containment for insulin to be delivered (not shown) in the insulin delivery device 620 via an infusion set coupled to a subcutaneously positioned cannula under the skin of the patient.

Figure 3:
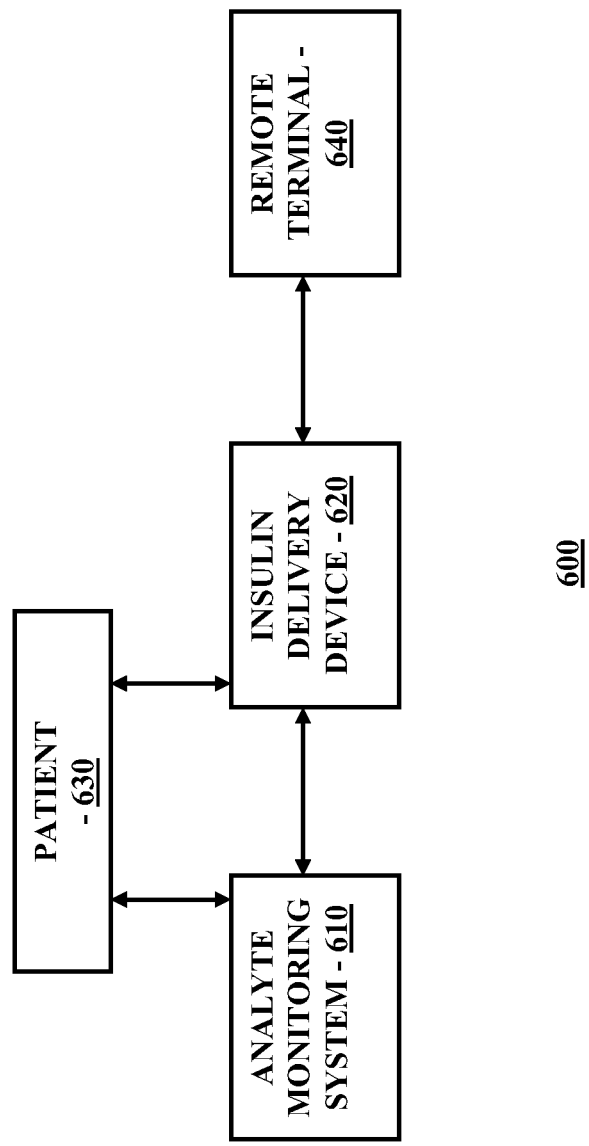
FIG. 3 is a block diagram illustrating an exemplary embodiment of an insulin therapy management system that incorporates the delivery device of FIG. 2.

Memory unit 740 may include one or more of a random access memory (RAM), read only memory (ROM), or any other types of data storage units that is configured to store data as well as program instructions for access by the processor 710 and execution to control the insulin delivery device 620 and/or to perform data processing based on data received from, e.g., an analyte monitoring system 610, a remote terminal 640 (HCP or caregiver), the patient 630 or any other data input source (see for example FIG. 3).

FIG. 3 is a block diagram illustrating an insulin therapy management system 600 that includes an insulin infusion device and an analyte monitoring system. The insulin therapy management system 600 includes an analyte monitoring system 610 operatively coupled to an insulin delivery device 620, which may be in turn, operatively coupled to a remote terminal 640. Analyte monitoring system 610 is, in one embodiment, coupled to the patient 630 so as to monitor or measure the analyte levels of the patient. Moreover, the insulin delivery device 620 is coupled to the patient using, for example, an infusion set and tubing connected to a cannula (not shown) that is placed transcutaneously through the skin of the patient so as to infuse medication such as, for example, insulin, to the patient.

In one embodiment, the analyte monitoring system 610 may include one or more analyte sensors subcutaneously positioned such that at least a portion of the analyte sensors are maintained in fluid contact with the patient's analytes. The analyte sensors may include, but not limited to short term subcutaneous analyte sensors or transdermal analyte sensors, for example, which are configured to detect analyte levels of a patient over a predetermined time period, and after which, a replacement of the sensors is necessary.

The one or more analyte sensors of the analyte monitoring system 610 is coupled to a respective one or more of a data transmitter unit which is configured to receive one or more signals from the respective analyte sensors corresponding to the detected analyte levels of the patient, and to transmit the information corresponding to the detected analyte levels to a receiver device, and/or insulin delivery device 620. That is, over a communication link, the transmitter units may be configured to transmit data associated with the detected analyte levels periodically, and/or intermittently and repeatedly to one or more other devices such as the insulin delivery device and/or the remote terminal 640 for further data processing and analysis. The transmitter units of the analyte monitoring system 610 may be, in one embodiment, configured to transmit the analyte related data substantially in real time to the insulin delivery device 620 and/or the remote terminal 640 after receiving it from the corresponding analyte sensors such that the analyte level such as glucose level of the patient 630 may be monitored in real time.

The transmitter units of the analyte monitoring system 610 may be configured to directly communicate with one or more of the remote terminal 640 or the insulin delivery device 620. Furthermore, within the scope of the present invention, additional devices may be provided for communication in the insulin therapy management system 600 including additional receiver/data processing unit, remote terminals (such as a HCP terminal and/or a bedside terminal in a hospital environment, for example).

The insulin delivery device 620 may include in one embodiment, but is not limited to, an external infusion device such as an external insulin infusion pump, an implantable pump, a pen-type insulin injector device, a patch pump, an inhalable infusion device for nasal insulin delivery, or any other type of suitable delivery system.

In one embodiment, the analyte monitoring system 610 includes a strip port configured to receive a test strip for capillary blood glucose testing. In one aspect, the glucose level measured using the test strip may in addition, be configured to provide periodic calibration of the analyte sensors of the analyte monitoring system 610 to assure and improve the accuracy of the analyte levels detected by the analyte sensors.

Exemplary in vitro and in vivo analyte monitoring system and drug infusion systems that may be adapted for the present invention include, but are not limited to, those described in U.S. Pat. Nos. 6,175,752; 6,329,161; 6,284,478; 6,916,159; 7,041,468; 7,077,328, and U.S. patent application Ser. Nos. 11/383,945; 11/365,168; 11/386,915; 11/396,181; 11/396,182, and elsewhere, the disclosures of which are herein incorporated in their entirety by reference.

According to aspects of the present invention, an alert and/or alarm 32 can also be shown on display 18 indicating, for example, whether the current measurement falls within a predetermined range, such as an ideal glucose range, an upper or lower range of moderate concern or an upper or lower range of high concern.

Figure 4:
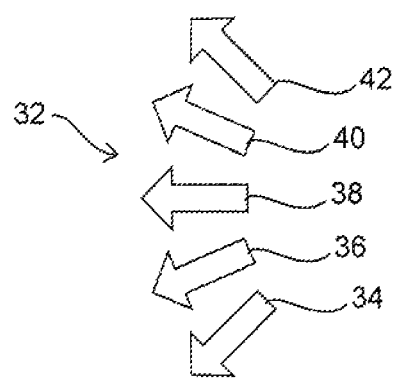
FIG. 4 is a detail example of various alert and alarm displays, one of which is shown in the system of FIG. 1.

Referring now to FIG. 4, a further example of alert and alarm displays 32 is shown. A steeply downwardly inclined arrow 34 (e.g. from about −60 to about −90 degrees) can be used to indicate a glucose reading in a lower range of high concern, such as below 50 mg/dL. A moderately downwardly inclined arrow 36 (e.g. from about −30 to about −45 degrees) can be used to indicate a glucose reading in a lower range of moderate concern, such as about 50 mg/dL to about 75 mg/dL. A horizontal arrow 38 (e.g. about 0 degrees) can be used to indicate a glucose reading in an ideal range, such as about 75 mg/dL to about 175 mg/dL. A moderately upwardly inclined arrow 40 (e.g. about 30 or about 45 degrees) can be used to indicate a glucose reading in an upper range of moderate concern, such as about 175 mg/dL to about 250 mg/dL. Finally, a steeply upwardly inclined arrow 42 (e.g. from about 60 to about 90 degrees) can be used to indicate a glucose reading in an upper range of high concern, such as above about 250 mg/dL. As previously indicated above, various other visual elements, and/or audible or physical indicators can be used to provide the user with an alert or an alarm.

Figure 5:
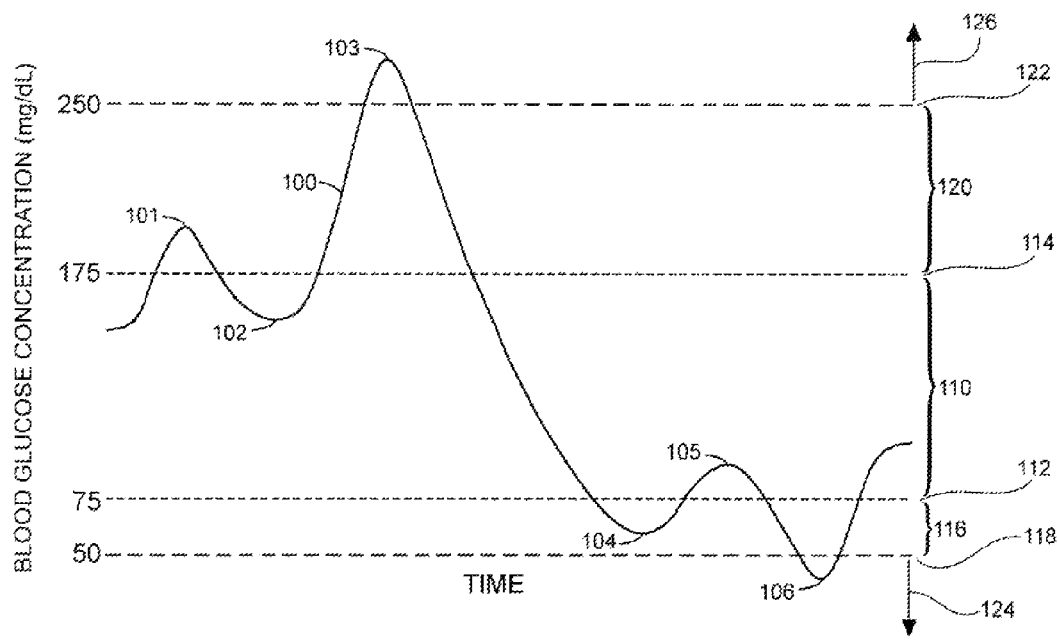
FIG. 5 is a graph depicting an example of how the glucose level of a user might vary over the course of a portion of a day.

Referring now to FIG. 5, an example of blood glucose values for a user is shown. Curve 100 depicts how the user's blood glucose might change with time over a portion of a day. In this example, the ideal range for the user is about 75 mg/dL to about 175 mg/dL, shown with reference numeral 110 and bounded by dashed lines 112 and 114. The ranges of moderate concern are about 50 mg/dL to about 75 mg/dL (lower alert zone 116, bounded by dashed lines 112 and 118) and about 175 mg/dL to about 250 mg/dL (upper alert zone 120, bounded by dashed lines 114 and 122). The ranges of high concern are below about 50 mg/dL (lower alarm zone 124, below dashed line 118) and above about 250 mg/dL (upper alarm zone 126, above dashed line 122).

In FIG. 5 the glucose values (100) begin at about 150 mg/dL, rise to about 195 mg/dL (101), fall to about 155 mg/dL (102), rise to about 270 mg/dL (103), fall to about 60 mg/dL (104), rise to about 90 mg/dL (105), fall to about 40 mg/dL (106), and end at about 100 mg/dL.

Figure 6:
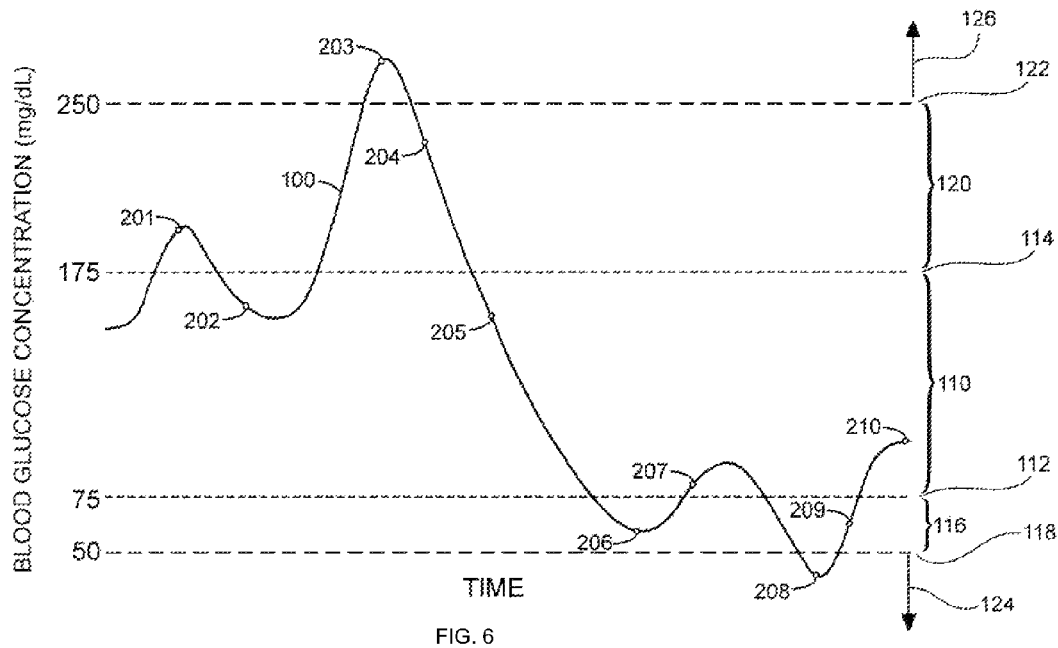
FIG. 6 is a graph depicting the glucose levels shown in FIG. 3 with testing points added, some of which occur as a result of a reminder (alert or alarm)

FIG. 6 shows the same blood glucose values 100 as FIG. 5 but adds the testing that was performed by that user, some of which occurs as a result of a reminder (alert and/or alarm and/or reminder). For example, after a light meal (snack) the user tests with a reading of 193 mg/dL (201) that falls in the upper alert zone (120). This reading may cause meter 12 to generate an alert to the user, e.g., flashing display, beep, or the like, that his or her glucose is in an upper level of moderate concern, as previously described above. The meter may alert the user substantially immediately after the determination of the reading in the upper alert zone, or sometime thereafter as described below. Regardless of whether the user is notified substantially immediately of a reading in an alert zone (or other zone of concern as described herein), the meter may also be configured to remind the user to perform a re-test after a predetermined amount of time following a reading in a zone of importance (alarm zone or alert zone). For example, after the above-described meter reading in upper alert zone 120, a meter reminder may notify the user to perform a test after a predetermined amount of time, e.g., about 5 minutes, e.g., about 10 minutes, e.g., about 20 minutes, e.g., about 30 minutes, etc., and may periodically remind a user until a test is performed or until the reminder is cleared by the user. For example, the user may respond to the reading and alert (if alerted) with modest therapy and some time later (e.g., about 30 minutes), a reminder prompts the user to test, resulting in a reading of 160 mg/dL (202) that falls in the ideal zone (110).

Later, after a large meal the user tests with a reading of 268 mg/dL (203) that falls in the upper alarm zone (126). This reading causes meter 12 to generate an alarm to the user that his or her glucose is in an upper level of high concern. The user responds to the reading with an appropriate therapy and some time later (e.g. 20 minutes), a reminder prompts the user to test, resulting in a reading of 232 mg/dL (204) that falls in the upper alert zone (120). This reading causes meter 12 to generate an alert to the user that his or her glucose is in an upper level of moderate concern. The user may note that the previous therapy was appropriate and again, some time later (e.g. 30 minutes), a reminder prompts the user to test again, resulting in a reading of 156 mg/dL (205) that falls in the ideal zone (110) and confirms the previous therapy was appropriate.

Still later, after having exercised but not having eaten the user feels slightly symptomatic and tests with a reading of 61 mg/dL (206) that falls in the lower alert zone (116). This reading causes meter 12 to generate an alert to the user that his or her glucose is in a lower level of moderate concern. The user responds by eating a light meal (snack) and some time later (e.g. 25 minutes), a reminder prompts the user to test, resulting in a reading of 81 mg/dL (207) that falls in the ideal zone (110).

Yet later still, the user feels symptomatic and tests with a reading of 41 mg/dL (208) that falls in the lower alarm zone (124). This reading causes meter 12 to generate an alarm indicating that the glucose level is in a lower level of high concern. The user responds by eating a modest meal and some time later (e.g. 15 minutes), a reminder prompts the user to test, resulting in a reading of 63 mg/dL (209) that falls in the lower alert zone (116). This reading causes meter 12 to generate an alert indicating that the glucose level is now in a lower level of moderate concern. The user may note that the previous therapy (meal) was appropriate or may eat a small amount (snack) and again some time later (e.g. 25 minutes), a reminder prompts the user to test, resulting in a reading of 99 mg/dL (210) that falls in the ideal zone (110) and confirms the course of therapy was appropriate.

It should be noted that in this example, tests 201, 203, 206 and 208 were initiated by the user based on events known by the user to cause changes in blood glucose, or based on symptoms experienced by the user. More importantly, the user was prompted to perform tests 202, 204, 205, 207, 209 and 210 by a meter constructed according to aspects of the present invention. These prompts or timed reminders assist the user in performing appropriate tests in a timely manner. These tests in turn facilitate the user's important goal of keeping his or her blood glucose level in the ideal zone 110 to maintain the user's short-term and long-term health.

Embodiments also include supervisor-controllable, including person-restrictive (e.g., user-restrictive), medical devices. Configurations of a medical device may be settable and/or lockable by a supervisor (e.g., a HCP, parent or guardian, caregiver, or the like), e.g., remotely or by direct action (e.g., using a user interface of the device, or the like). For example, certain configurations of a medical device may be settable and/or lockable by a first person (e.g., a HCP) having a first access level (e.g., full access such as full Read/Write permission) and certain configurations that may be settable and/or lockable by a second person (e.g., a caregiver) having a second access level (e.g., limited Read/Write permission). The medical device may be settable and/or lockable by a third person (e.g., a user under the supervision of the first and second persons) having a third access level (e.g., further limited, e.g., Read only—including no rights to modify previously inputted data). Any number of persons may have certain or limited access rights to a medical device. For example, certain embodiments include medical devices having certain configurations settable and/or lockable by a HCP and certain other features settable and/or lockable by a caregiver. A user may be completely restricted from modifying the configurations set by the HCP and/or caregiver.

Configurations may be access controlled with an access code (e.g., password protected, voice authentication, USB token protected, or other manner of authenticating a user) to allow access permissions for a specific individual, medical device, computer, or group of individuals. When permission is set, the type and level of access granted to an individual, computer, or group is granted. For example, various degrees of, e.g., Read and Write and View permissions may be granted to different persons, as described above.

Different codes may provide different rights. For example an HCP code may enable a HCP to enter prescriptive information and/or delete and/or modify stored prescriptive ("Rx") information, where prescriptive information is broadly defined relevant information prescribed by a HCP. Prescriptive information may include patient-specific data and may include but is not limited to, one or a plurality of basal rates, insulin ideal analyte ranges, alert and alarm thresholds, medication type (e.g., insulin type), medication dose including total daily dose (e.g., total daily insulin dosage), drug sensitivity (e.g., insulin sensitivity), when to take a medication, how to take a medication, when to treat a condition, how to treat a condition, when to elevate concerns to a HCP or caregiver, reminder schemes (e.g., setting times of reminders), etc. The above is not an exhaustive list, e.g., for treating diabetes, information may also include insulin/carbohydrate information, and other relevant information. In this manner, a medical device may be customizable by a HCP to include user-specific prescriptive information, some of which may not relate to values or settings in the medical device but may be made available for reference purposes only (e.g., as a text note such as those commonly displayed on a PDA, or the like). A medical device may be lockable by a HCP, who may also set access levels for others such as for a caregiver and/or user. In this manner, a HCP (or other designated individual) may serve as the "Administrator" having the ability to control access at a granular level, establishing access levels on a person-by-person basis.

In addition to, or instead of HCP provided configurations, a caregiver may also enter and/or lock configurations of a medical device. In many embodiments, at least some of the configurations under caregiver control differ at least in part from configurations reserved for HCP control, which would be prescriptive in nature, as described above. Caregiver access may enable a caregiver to enter caregiver information and/or delete and/or modify stored caregiver information. Caregiver information includes, but is not limited to the ability to set and lock any value or user restriction not previously set and locked by the HCP such as non-prescriptive alarm values, user menu access, and other user privileges such as data transfer (e.g., upload to a PC) and storage options (e.g., read-only or read-write access to various data). For example, a HCP may set and lock values and allowed options (e.g., lock menus). The caregiver access allowed by the HCP can set and lock that which the HCP did not lock. Caregiver access may provide the caregiver with the ability to lock and/or unlock user features, such as providing the user with increased access over time as the user begins to understand and appreciate the subtleties and complexities of various features (e.g., setting correct values such as alarm thresholds and reminder time values or accessing menus that show information that might be confusing if not interpreted properly). Similarly, the user may be able to access that allowed by the caregiver (and HCP), and may be able to set that which is not locked.

The configurations may be set and/or locked by inputting data directly into the medical device using, e.g., a user interface, or may be accomplished indirectly including remotely, e.g., via a computer system connected to a network, where a network represents any uni- or bi-directional communication link suitable for communicating data, such as a wide-area network, local area network, or a global computer network like the World Wide Web ("the Web"). Accordingly, embodiments include a web-based data management system that allows persons to controllably access and/or manipulate and/or share information, depending on a given person's permission level. Each HCP and/or caregiver and/or medical device user may interact with a computing device suitable for accessing the data management system via a network. For example, a personal computer, laptop computer, phone such as a cellular telephone, a personal digital assistant (PDA), etc., may be used. The communication device typically executes communication software, typically a web browser such as INTERNET EXPLORER from Microsoft Corporation of Redmond, Wash., or the like, in order to communicate with the data management system.

Once configurations are set, e.g., by a HCP, caregiver or user, the stored information may be employed by the medical device in the execution of healthcare management, e.g., glucose monitoring. The stored information may be conveyed to a user in audible format and/or visual and/or tactile format. For example, prescriptive information inputted by a HCP may be visually displayed on the display of a medical device, e.g., as an icon (e.g., an "Rx" icon, as a note (similar to displayed PDF notes), or the like), or may be in audible or tactile form.

Figure 7A:
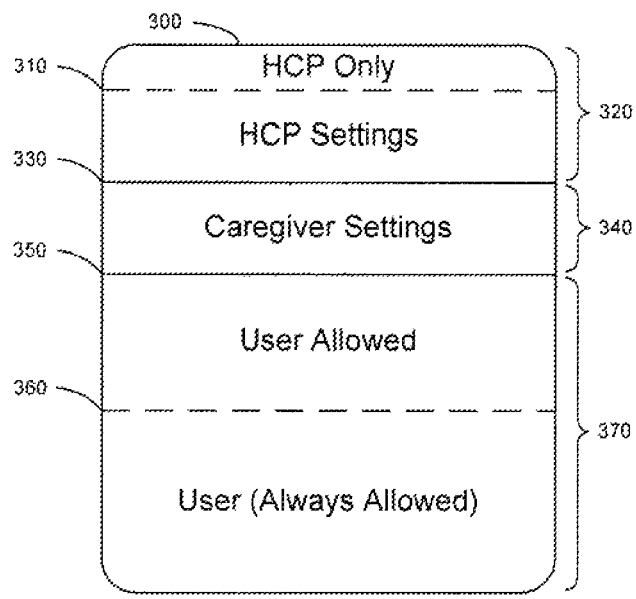
FIGS. 7A and 7B show exemplary embodiments of a medical device with restrictive user control.

FIG. 7A shows the hierarchal permission scheme of an embodiment of a medical device 300 having restrictive control, e.g., restrictive caregiver and user control. The most critical settings and portions of the user interface (e.g. the ability to set values and activate menu items) may be set by a HCP. Values that must be prescribed by a HCP are in the HCP Only portion of the user interface as bounded by the dashed line 310. Additional values prescribed by the HCP are included in the HCP settings region 320 as bounded by the solid line 330. For example, the HCP may restrict access to various options and menus (e.g., data transfer and storage parameters) and may set and lock various values such as, for example, the lower threshold for high concern and the associated alarm parameters. A caregiver (e.g. a parent) may set additional restrictions by the Caregiver settings region 340 as bounded by the solid line 350. For example, the caregiver may set and lock the previously unlocked upper threshold for high concern and the associated alarm parameters and set preferred values for other threshold and the associated alarm parameters without locking those values (i.e., the user may update those values at a later time). Finally, the user of the medical device is allowed access to the User Allowed portion of the user interface as bounded by the dashed line 360 along with a portion of the user interface that is always allowed, which is included in the User region 370 of the user interface.

Figure 7B:
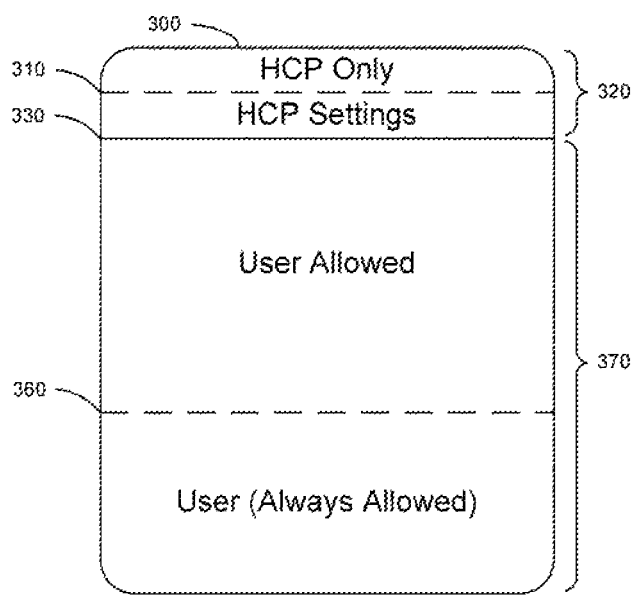

FIG. 7B shows medical device 300 of FIG. 7A, but in this embodiments there is no caregiver and the User region 370 includes of all portions of the user interface that are not restricted by the HCP in the HCP settings region 320.

Figure 8:
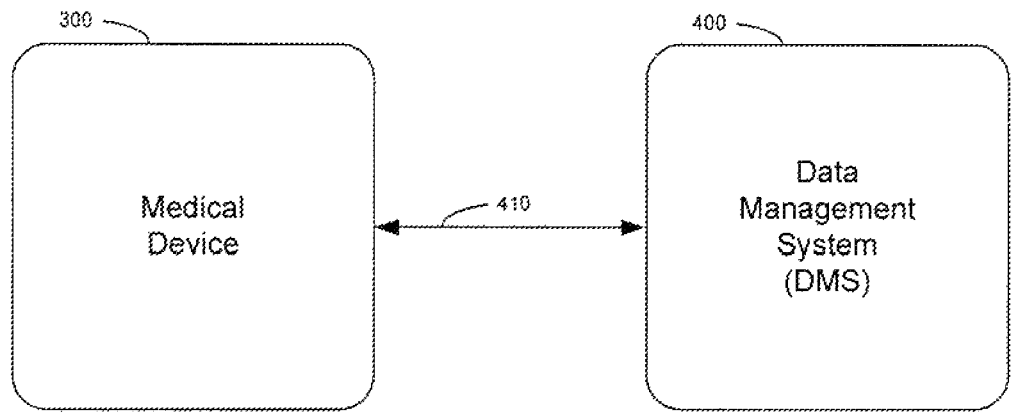
FIG. 8 shows the medical device of FIG. 7B connected to an exemplary embodiment of a data management system.

FIG. 8 shows medical device 300 as connected to a Data Management System (DMS) 400 through connection 410 which may be wired or wireless. The DMS 400 may interface to many medical devices where only one is shown, and each may be of similar or differing types (e.g. analyte meter (such as a blood glucose meter), continuous analyte monitor (such as a continuous glucose monitor), or drug infusion pump (such as an insulin pump)).

Figure 9:
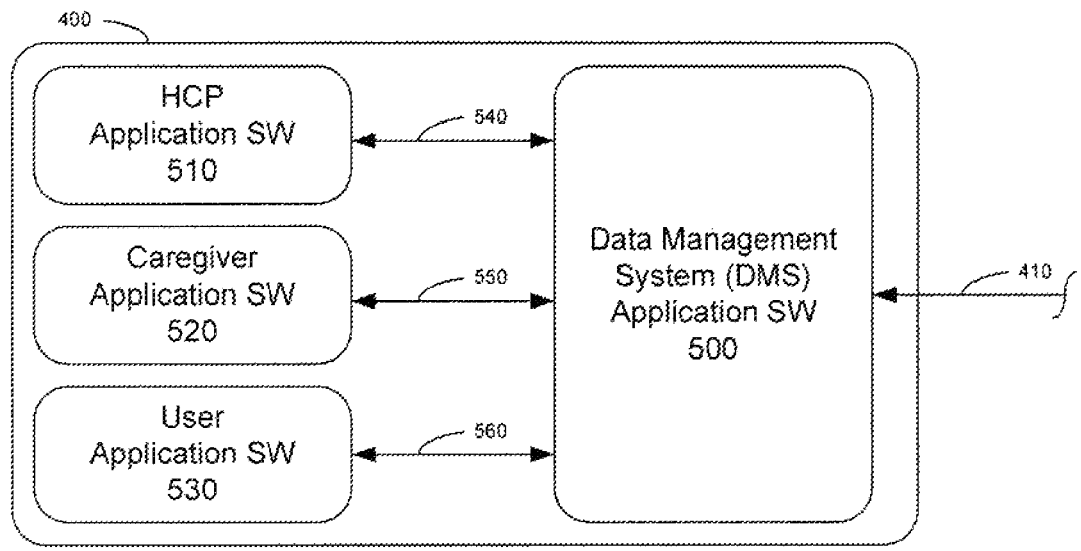
FIG. 9 shows an exemplary embodiment of application software that may run on the data management system of FIG. 8.

FIG. 9 shows application software (SW) that runs on the DMS 400 where the DMS Application SW 500 interfaces to the medical device (not shown) via connection 410. SW 500 may be embodied on a computer readable medium. The DMS Application SW 500 also interfaces to the HCP Application SW 510, the Caregiver Application SW 520, and the User Application SW 530 through SW connections 540, 550 and 560 respectively. Each of the HCP, Caregiver and User Application SW modules has the same restrictive user controls (e.g. privileges and restrictions) to those that are set directly on the medical device while allowing a more complete user interface, such as a Graphical User Interface (GUI) such as those commonly found on PC computers. Additional features available only on the DMS 400 through the GUI (e.g. advanced data graphing features) may also be subject to similar restrictive user controls as described for the medical device.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "an," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A medical system comprising:
a glucose monitoring device;
an insulin pump; and
a data management system in communication with the glucose monitoring device and the insulin pump, the data management system having a memory including programming of an access level hierarchy that enables a plurality of individuals to have different access level rights to enter, modify and lock parameters of the glucose monitoring device and the insulin pump, the access level hierarchy including at least a first, a second, and a third access level;
   wherein first access level rights enable a healthcare professional having first access level rights to set, modify and lock prescriptive parameters and non-prescriptive parameters of the glucose monitoring device and the insulin pump;
   wherein second access level rights enable a caregiver having second access level rights to set, modify and lock the non-prescriptive parameters of the glucose monitoring device and the insulin pump that have not been locked by the healthcare professional;
   wherein the second access level rights preclude the caregiver from setting, modifying and locking the prescriptive parameters of the glucose monitoring device and the insulin pump;
   wherein third access level rights enable a user having third access level rights to set, modify and lock the non-prescriptive parameters of the glucose monitoring device and the insulin pump that have not been locked by the healthcare professional or the caregiver; and
   wherein the third access level rights preclude the user from setting, modifying and locking the prescriptive parameters of the glucose monitoring device and the insulin pump.

2. A medical system comprising:
a medical device for monitoring an analyte;
a medical device for infusing an agent into a user;
wherein the medical devices each include a memory with programming of an access level hierarchy that enables a plurality of individuals, including the user, to have different access level rights to set and modify parameters of the medical devices, the access level hierarchy including at least a first, a second, and a third access level, wherein first access level rights enable a healthcare professional having first access level rights to set, modify and lock prescriptive parameters and non-prescriptive parameters of the medical devices, wherein second access level rights enable a caregiver having second access level rights to set, modify and lock the non-prescriptive parameters of the medical devices that have not been locked by the healthcare professional, wherein the second access level rights preclude the caregiver from setting, modifying and locking the prescriptive parameters of the medical devices, wherein third access level rights enable the user having third access level rights to set, modify and lock the non-prescriptive parameters of the medical devices that have not been locked by the healthcare professional or the caregiver, and wherein the third access level rights preclude the user from setting, modifying and locking the prescriptive parameters of the medical devices; and
a data communication unit directly operable by each of the plurality of individuals.

3. The medical system of claim 2 wherein the data communication unit comprises a user interface coupled to one or both of the medical devices.

4. The medical system of claim 2 wherein the data communication unit is configured for remotely controlling one or both of the medical devices.

5. The medical system of claim 4 wherein the data communication unit comprises a networked computer system.

6. The medical system of claim 2 wherein each of the plurality of individuals is assigned an access code enabling each individual to set and modify parameters according to the access level hierarchy.

7. The medical system of claim 2 further comprising a data management system.

8. The medical system of claim 2 wherein at least one of the parameters comprises a reminder for reminding the user to take a diagnostic action.

9. The medical system of claim 2 wherein at least one of the parameters comprises infusion information.

10. The medical system of claim 9 wherein the infusion information comprises bolus information.

11. The medical system of claim 2 wherein the system is configured to enable the healthcare professional to remotely convey notes to the user via one or both of the medical devices.

12. The medical system of claim 2 wherein the agent is insulin.

13. The medical system of claim 2 wherein the analyte is glucose.

14. The medical system of claim 8 wherein the diagnostic action is to measure a level of the analyte.

15. The medical system of claim 3 wherein the user interface is configured to communicate an alarm, an alert or a reminder.

16. The medical system of claim 1 wherein at least one of the parameters comprises a reminder for reminding the user to take a diagnostic action.

17. The medical system of claim 16 wherein the diagnostic action is to measure the user's glucose level.

18. The medical system of claim 1 wherein the non-prescriptive parameters include at least one non-prescriptive alarm threshold value configured to trigger an alarm, an alert or a reminder.

19. A method of controlling access to a medical system comprising at least one medical device and a data communication unit operable by each of a plurality of individuals including a healthcare professional, a caregiver and a user, the method comprising:
configuring the at least one medical device with an access level hierarchy that enables the plurality of individuals to have different access level rights to set and modify parameters of the at least one medical device, the access level hierarchy including at least a first, a second, and a third access level, wherein first access level rights enable the healthcare professional having first access level rights to set, modify and lock prescriptive parameters and non-prescriptive parameters of the at least one medical device, wherein second access level rights enable the caregiver having second access level rights to set, modify and lock non-prescriptive parameters of the at least one medical device that have not been locked by the healthcare professional, wherein the second access level rights preclude the caregiver from setting, modifying and locking prescriptive parameters of the at least one medical device, wherein third access level rights enable a user having third access level rights to set, modify and lock the non-prescriptive parameters of the at least one medical device that have not been locked by the healthcare professional or the caregiver, and wherein the third access level rights preclude the user from setting, modifying and locking the prescriptive parameters of the at least one medical device.

20. The system of claim 1 wherein the prescriptive parameters include one or more of a basal rate, an insulin ideal analyte range, an alert or alarm threshold, a medication type, a medication dose, a total daily medication dose, a drug sensitivity, a parameter associated with when to take medication, a parameter associated with how to take the medication, a parameter associated with when to treat a condition, a parameter associated with how to treat the condition, a reminder scheme, or any combination thereof.

21. The system of claim 1 wherein the non-prescriptive parameters include one or more of a non-prescriptive alarm value, a user menu access parameter, a data transfer and storage parameter, or any combination thereof.

22. The system of claim 2 wherein the prescriptive parameters include one or more of a basal rate, an insulin ideal analyte range, an alert or alarm threshold, a medication type, a medication dose, a total daily medication dose, a drug sensitivity, a parameter associated with when to take medication, a parameter associated with how to take the medication, a parameter associated with when to treat a condition, a parameter associated with how to treat the condition, a reminder scheme, or any combination thereof.

23. The system of claim 2 wherein the non-prescriptive parameters include one or more of a non-prescriptive alarm value, a user menu access parameter, a data transfer and storage parameter, or any combination thereof.

24. The system of claim 1 wherein the user is completely restricted from modifying the parameters set by the healthcare professional and the caregiver.

25. The system of claim 1 wherein each of the access levels is password protected.

26. The system of claim 1 wherein each of the access levels is token protected.

27. The system of claim 1 wherein the data management system includes a web-based data management system.

28. The system of claim 27 wherein the web-based data management system can be accessed through a personal computer or laptop computer.

29. The system of claim 27 wherein the web-based data management system can be accessed through a cellular telephone.

* * * * *

UNITED STATES PATENT AND TRADEMARK OFFICE
CERTIFICATE OF CORRECTION

PATENT NO. : 8,579,853 B2  
APPLICATION NO. : 11/555207  
DATED : November 12, 2013  
INVENTOR(S) : Christopher V. Reggiardo et al.

Page 1 of 1

It is certified that error appears in the above-identified patent and that said Letters Patent is hereby corrected as shown below:

In the Claims:
(Column 16, line 3) Claim 19, line 17, replace "lock non-prescriptive" with --lock the non-prescriptive--
(Column 16, line 7) Claim 19, line 21, replace "locking prescriptive" with --locking the prescriptive--

Signed and Sealed this
Twenty-ninth Day of July, 2014

Michelle K. Lee
*Deputy Director of the United States Patent and Trademark Office*